(12) United States Patent
Czernichow et al.

(10) Patent No.: US 10,167,450 B2
(45) Date of Patent: Jan. 1, 2019

(54) HUMAN PANCREATIC BETA CELL LINES FOR DIAGNOSTIC OF DIABETES

(75) Inventors: Paul Czernichow, Paris (FR); Raphaël Scharfmann, Paris (FR); Philippe Ravassard, Paris (FR)

(73) Assignees: SARL ENDOCELLS, Paris (FR); INSTITUT NATIONAL DE LA SANTE ET DE LA RECHERCHE MEDICALE (INSERM), Paris (FR); CENTRE NATIONAL DE LA RECHERCHE SCIENTIFIQUE (CNRS), Paris (FR)

( * ) Notice: Subject to any disclaimer, the term of this patent is extended or adjusted under 35 U.S.C. 154(b) by 972 days.

(21) Appl. No.: 12/528,048

(22) PCT Filed: Feb. 21, 2008

(86) PCT No.: PCT/EP2008/052153
§ 371 (c)(1),
(2), (4) Date: Jul. 29, 2011

(87) PCT Pub. No.: WO2008/102000
PCT Pub. Date: Aug. 28, 2008

(65) Prior Publication Data
US 2011/0318389 A1    Dec. 29, 2011

Related U.S. Application Data

(60) Provisional application No. 60/890,936, filed on Feb. 21, 2007.

(51) Int. Cl.
*C12N 5/071* (2010.01)
*C12N 5/09* (2010.01)
*A61K 35/12* (2015.01)

(52) U.S. Cl.
CPC ......... *C12N 5/0676* (2013.01); *C12N 5/0693* (2013.01); *A61K 35/12* (2013.01); *C12N 2500/90* (2013.01); *C12N 2503/00* (2013.01); *C12N 2503/02* (2013.01); *C12N 2510/00* (2013.01); *C12N 2510/04* (2013.01); *C12N 2533/52* (2013.01); *C12N 2533/90* (2013.01); *G01N 2800/042* (2013.01)

(58) Field of Classification Search
CPC .................................................. C12N 5/0676
See application file for complete search history.

(56) References Cited

U.S. PATENT DOCUMENTS 5,786,221 A     7/1998  Ma et al.
2005/0123521 A1  6/2005  Zern et al.

FOREIGN PATENT DOCUMENTS

WO     WO 03/033685 A2      4/2003
WO     WO 2003/033685   *   4/2003

OTHER PUBLICATIONS

Czernichov et al., IDS Jul. 29, 2011, A3.*
Bittscheidt et al. (2004) Impact of donor-recipient MHC matching on experimental islet allotransplant survival in naïve and presensitized Lewis rats. Transplantation 78: 162-164.*
Greiner et al. (1998) SCID mouse models of human stem cell engraftment. Stem Cells 16: 166-177.*
Loudovaris et al. (1999) Correction of diabetic nod mice with insulinomas implanted within Baxter immunoisolation devices. Journal of Molecular Medicine 77: 219-222.*
Meglasson et al. (1986) Glucose transport by radiation-induced insulinoma and clonal pancreatic beta-cells. Diabetes 35: 1340-1344.*
Narushima et al. (2005) A human beta-cell line for transplantation therapy to control type 1 diabetes. Nature Biotechnology 23(10): 1274-1282.*
Lightfoot et al., 2013, PLoS One, vol. 6(6), pp. 1-12.*
Akagi et al. (1981, Cancer, vol. 47, pp. 417-424).*
Perryman LE (2004, Vet. Pathol., vol. 41, pp. 95-100).*
Mashimo et al. (2012, Cell Reports, vol. 2, pp. 685-694).*
International Search Report issued in application No. PCT/EP2008/052153 dated Jun. 23, 2008.
Apelqvist et al., "Notch signaling controls pancreatic cell differentiation," Nature, Aug. 1999, pp. 877-881, vol. 400.
Asfari et al., "Establishment of 2-Mercaptoethanol-Dependent Differentiated Insulin-Secreting Cell Lines," Endocrinology, 1992, pp. 167-178, vol. 130, No. 1.
Assady et al., Insulin Production by Human embryonic Stem Cells, Diabetes, Aug. 2001, pp. 1691-1697, vol. 50.
Basmaciogullari et al., "Pancreatic pattern of expression of thyrotropin-releasing hormone during rate embryonic development," J. Endocrinol., 2000, pp. 481-488, vol. 166.
Blyszczuk et al., "Expression of Pax4 in embryonic stem cells promotes differentiation of nestin-positive progenitor and insulin-producing cells," PNAS, Feb. 2003, pp. 998-1003, vol. 100, No. 3.
Bollheimer et al., "Glucagon production of the rat insulinoma cell line INS-1—A quantitative comparison with primary rat pancreatic islets," Biochem. Biophys. Res. Commun., 2005, pp. 327-332, vol. 330.
Bottazzo et al., "Islet-Cell Antibodies in Diabetes Mellitus with Autoimmune Polyendocrine Deficiencies," The Lancet, Nov. 1974, pp. 1279-1283.
Brolén et al., "Signals From the Embryonic Mouse Pancreas Induce Differentiation of Human Embryonic Stem Cells Into Insulin-Producing β-Cell-Like Cells," Diabetes, Oct. 2005, pp. 2867-2874, vol. 54.

(Continued)

Primary Examiner — Thaian N Ton
Assistant Examiner — David A. Montanari
(74) Attorney, Agent, or Firm — Foley & Lardner LLP

(57) ABSTRACT

The present invention relates to a method for preparing commercial scale quantities of human functional Betacells and to the establishment of cell lines. It also relates to a method of diagnosis using Beta cell tumors or cells derived thereof. The method comprises sub-transplantation procedure to enrich the graft in proliferating Betacells, allowing to generate human Betacell lines. Such lines express little amount of insulin and have a gene expression profile that resembles to adult Betacells. In addition, the human Betacell lines are able to normalize glycemia of diabetic mice when transplanted, demonstrating their insulin secretion capabilities.

9 Claims, 13 Drawing Sheets

Figure 1:
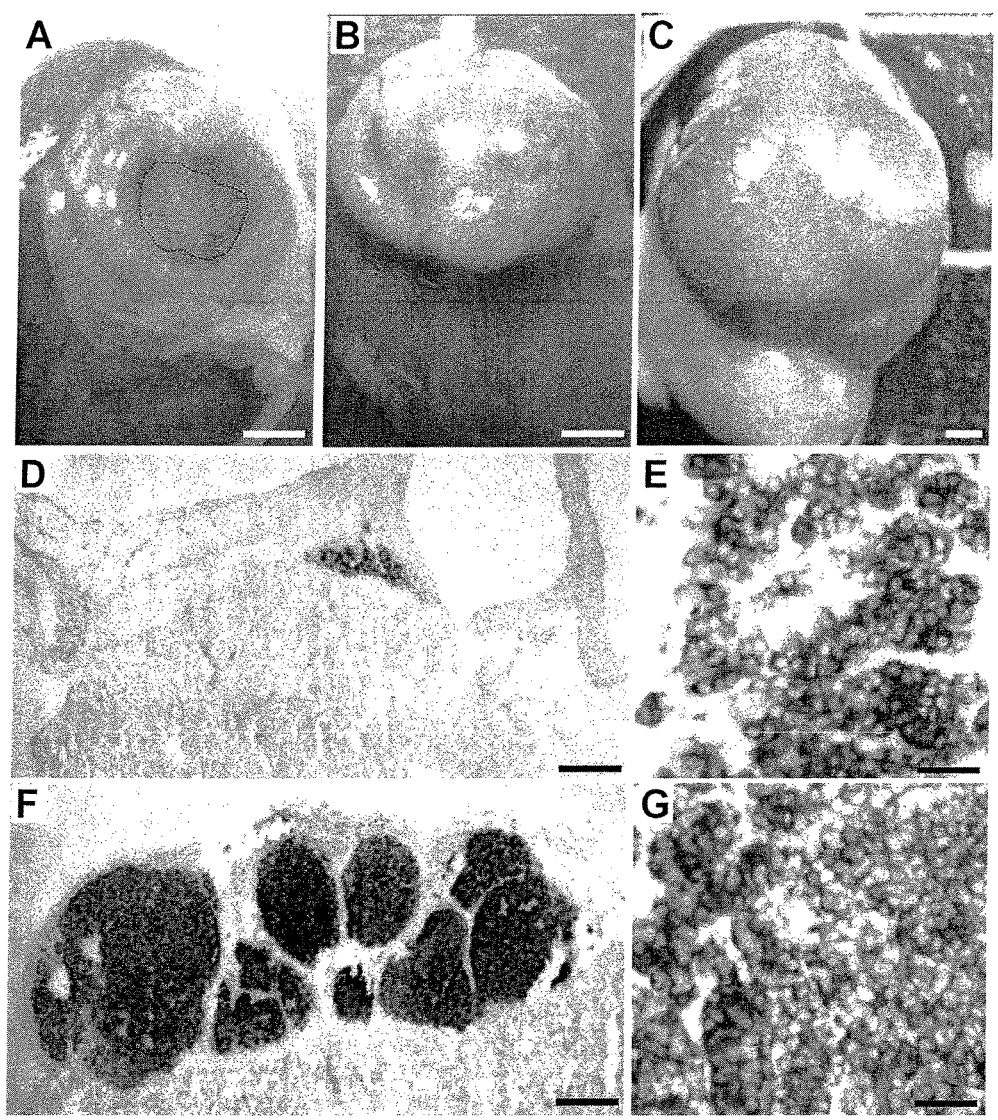

Specification includes a Sequence Listing.

(56) References Cited

OTHER PUBLICATIONS

Brun et al., "The diabetes-linked transcription factor PAX4 promotes β-cell proliferation and survival in rat and human islets," J. Cell Biol., Dec. 2004, pp. 1123-1135, vol. 167, No. 6.
Castaing et al., "Blood glucose normalization upon transplantation of human embryonic pancreas into beta-cell-deficient SCID mice," Diabetologia, 2001, pp. 2066-2076, vol. 44.
Castaing et al., "Efficient restricted gene expression in beta cells by lentivirus-mediated gene transfer into pancreatic stem/progenitor cells," Diabetologia, 2005, pp. 709-719, vol. 48.
Castaing et al., "Ex Vivo Analysis of Acinar and endocrine Cell Development in the Human Embryonic Pancreas," Developmental Dynamics, 2005, pp. 339-345, vol. 234.
D'Amour et al., "Production of pancreatic hormone-expressing endocrine cells from human embryonic stem cells," Nature Biotechnol., Nov. 2006, pp. 1392-1401, vol. 24, No. 11.
De La Tour et al., "β-Cell Differentiation from a Human Pancreatic Cell Line in Vitro and in Vivo," Molecular Endocrinology, 2001, pp. 476-483, vol. 15, No. 3.
Delplanque et al., "Epithelial stem cell-mediated development of the human respiratory mucosa in SCID mice," J. Cell Science, 2000, pp. 767-778, vol. 113.
Demeterco et al., "c-Myc Controls Proliferation Versus Differentiation in Human Pancreatic Endocrine Cells," J. Clin. Endocrinol. & Metab., Jul. 2002, pp. 3475-3485, vol. 87, No. 7.
Duvilliéet al., "Label-Retaining Cells in the Rat Pancreas: Location and Differentiation Potential in Vitro," Diabetes, Aug. 2003, pp. 2035-2042, vol. 52.
Edlund H., "Transcribing Pancreas," Diabetes, Dec. 1998, pp. 1817-1823, vol. 47.
Efrat et al., "Beta-cell lines derived from transgenic mice expressing a hybrid insulin gene-oncogene," Proc. Natl. Acad. Sci. USA, Dec. 1988, pp. 9037-9041, vol. 85.
Efrat et al., "Conditional transformation of a pancreatic β-cell line derived from transgenic mice expressing a tetracycline-regulated oncogene," Proc. Natl. Acad. Sci. USA, Apr. 1995, pp. 3576-3580, vol. 92.
Efrat et al., "Murine Insulinoma Cell Line With Normal Glucose-Regulated Insulin Secretion," Diabetes, Jun. 1993, pp. 901-907, vol. 42.
Falorni et al., "Radioimmunoassays for glutamic acid decarboxylase (GAD65) and GAD65 autoantibodies using $^{35}$S or $^{3}$H recombinant human ligands," J. Immunol. Methods, 1995, pp. 89-99, vol. 186.
Gazdar et al., "Continuous, clonal, insulin- and somatostatin-secreting cell lines established from a transplantable rat islet cell tumor," Proc. Natl. Acad. Sci. USA, Jun. 1980, pp. 3519-3523, vol. 77, No. 6.
Gueli et al., "In vitro growth of a cell line originated from a human insulinoma," J. Exp. Clin. Cancer Res., 1987, pp. 281-285, vol. 6, No. 4.
Halban et al., "Gene and Cell-Replacement Therapy in the Treatment of Type 1 Diabetes," Diabetes, Oct. 2001, pp. 2181-2191, vol. 50.
Hanahan D., "Heritable formation of pancreatic β-cell tumours in transgenic mice expressing recombinant insulin/simian virus 40 oncogenes," Nature, May 1985, pp. 115-122, vol. 315.
Hansson et al., "Artifactual Insulin Release From Differentiated Embryonic Stem Cells," Diabetes, Oct. 2004, pp. 2603-2609, vol. 53.
Hori et al., "Growth inhibitors promote differentiation of insulin-producing tissue from embryonic stem cells," PNAS, Dec. 2002, pp. 16105-16110, vol. 99, No. 25.
Ju et al., "Transduction of non-dividing adult human pancreatic beta cells by an integrating lentiviral vector," Diabetologia, 1998, pp. 736-739, vol. 41.
Knaack et al., "Clonal Insulinoma Cell Line That Stably Maintains Correct Glucose Responsiveness," Diabetes, Dec. 1994, pp. 1413-1417, vol. 43.
Kobayashi N., "Cell therapy for Diabetes Mellitus," Cell Transplantation, 2006, pp. 849-854, vol. 15.
Levine et al., "Development of a Cell Line From the Human Fetal Pancreas," Transplantation Proceedings, Dec. 1995, p. 3410, vol. 27, No. 6.
Levy et al., "Optimised retroviral infection of human epidermal keratinocytes: long-term expression of transduced integrin gene following grafting on to SCID mice," Gene Therapy, 1998, pp. 913-922, vol. 5.
Lumelsky et al., "Differentiation of Embryonic Stem Cells to Insulin-Secreting Structures Similar to Pancreatic Islets," Science, May 2001, pp. 1389-1394, vol. 292.
Martin et al., "Preservation of Functioning Human Thyroid Organoids in the scid Mouse: 1. System Characterization," J. Clin. Endocrinol. And Metabol., 1993, pp. 305-310, vol. 77, No. 2.
Miralles et al., "Follistatin regulates the relative proportions of endocrine versus exocrine tissue during pancreatic development," Development, 1998, pp. 1017-1024, vol. 125.
Miyazaki et al., "Establishment of a Pancreatic β Cell Line That Retains Glucos-Inducible Insulin Secretion: Special Reference to Expression of Glucose Transporter Isoforms," Endocrinology, 1990, pp. 126-132, vol. 127, No. 1.
Narushima et al., "A human β-cell line for transplantation therapy to control type 1 diabetes," Nature Biotechnology, Oct. 2005, pp. 1274-1282, vol. 23, No. 10.
Palmer J.P., "Predicting IDDM: Use of humoral immune markers," Diabetes Reviews, Spring 1993, pp. 104-114, vol. 1, No. 1.
Rajagopal et al., "Insulin Staining of ES Cell Progeny from Insulin Uptake," Science, Jan. 2003, p. 363, vol. 299.
Santerre et al., "Insulin synthesis in a clonal cell line of simian virus 40-transformed hamster pancreatic beta cells," Proc. Natl. Acad. Sci. USA, Jul. 1981, pp. 4339-4343, vol. 78, No. 7.
Sladek et al., "A genome-wide association study identifies novel risk loci for type 2 diabetes," Nature, Feb. 2007, pp. 881-885, vol. 445.
Soldevila et al., "Transfection with SV40 Gene of Human Pancreatic Endocrine Cells," J. Autoimmunity, 1991, pp. 381-396, vol. 4.
Soria et al., "Insulin-Secreting Cells Derived From Embryonic Stem Cells Normalize Glycemia in Streptozotocin-Induced diabetic Mice," Diabetes, Feb. 2000, pp. 1-6, vol. 49.
Sosa-Pineda et al., "The Pax4 gene is essential for differentiation of insulin-producing β cells in the mammalian pancreas," Nature, Mar. 1997, pp. 399-402, vol. 386.
Thomas et al., "Adrenocortical tissue formed by transplantation of normal clones of bovine adrenocortical cells in scid mice replaces the essential functions of the animals' adrenal glands," Nature Medicine, Sep. 1997, pp. 978-983, vol. 3, No. 9.
Weissman et al., "Preliminary Experience with Subcutaneous Human Ovarian Cortex Transplantation in the NOD-SCID Mouse," Biol. of Reproduction, 1999, pp. 1462-1467, vol. 60.
Wenzlau et al., "The cation efflux transporter ZnT8 (SIc30A8) is a major autoantigen in human type 1 diabetes," PNAS, Oct. 2007, pp. 17040-17045, vol. 104, No. 43.
Zennou et al., "HIV-1 Genome Nuclear Import Is Mediated by a Central DNA Flap," Cell, Apr. 2000, pp. 173-185, vol. 101.
Zufferey et al., "Multiply attenuated lentiviral vector achieves efficient gene delivery in vivo," Nature Biotechnology, Sep. 1997, pp. 871-875, vol. 15.
Pihoker, Catherine et al., "Autoantibodies in Diabetes", Diabetes, Dec. 2005, pp. S52-S61, vol. 54, Supplement 2.
Renner, et al., "Replicating Retroviral Vectors for Gene Therapy of Solid Tumors," Novel Gene Therapy Approaches, 2013, pp. 129-156, Chapter 7.
Weir, et al., "Finally! A human pancreatic β cell line," Journal of Clinical Investigation, Sep. 2011, pp. 3395-3397, vol. 121, No. 9.
Dufayet, et al., "β-Cell Differetiation from a Human Pancreatic Cell Line in Vitro and in Vivo," Molecular Endocrinology, 2001, pp. 476-483, vol. 15.
Lightfoot, et al., "Understanding and Preventing Beta Cell Destruction: Protection Provided by $mt\text{-}ND2^a$," 2012, pp. 1-133, (Dissertation presentation).
Salmon, et al., "Reversible Immortalization of Human Primary Cells by Lentivector-Mediated Transfer of Specific Genes," Molecular Therapy, Oct. 2000, pp. 404-414, vol. 2, No. 4.

(56) References Cited

OTHER PUBLICATIONS

Efrat, et al., "Cell Cycle Regulation in Human Pancreatic Beta Cells," Stem Cell Therapy for Diabetes, 2010, pp. 86-103, Chapter 3.

* cited by examiner

HUMAN PANCREATIC BETA CELL LINES FOR DIAGNOSTIC OF DIABETES

The present invention relates to a method for preparing commercial scale quantities of human Beta cells and to the establishment of cell lines. It also relates to a method of diagnosis of diabetes using Beta cell tumors or cells derived thereof.

BACKGROUND OF THE INVENTION

Diabetes is a chronic disease that afflicts 200 millions people in the world. Type 1 diabetes results from autoimmune destruction of Beta cells, while type 2 diabetes is caused by a combination of insulin resistance and inadequate insulin secretion. Thus, in both type 1 and type 2 diabetes, the functional Beta cell mass is not sufficient to control glycemia. The mature pancreas contains two types of tissue: exocrine tissue composed of acinar cells that produce enzymes (e.g., carboxypeptidase-A) secreted via the pancreatic ducts into the intestine and endocrine islets composed of cells that produce hormones such as insulin (Beta cells), glucagon (alpha cells) somatostatin (delta cells) and pancreatic polypeptide (PP cells). Over the past decades research in the Beta cell field profited from the establishment of insulin-secreting cell lines, such as RIN and INS1 cells derived from x-ray induced rat insulinoma (Asfari et al., 1992; Gazdar et al., 1980), HIT cells generated by transformation of hamster islet cells by SV40 (Santerre et al., 1981) and BetaTC and Min6 cells derived from transgenic mice expressing SV40 T antigen under the control of the insulin promoter (Efrat et al., 1995; Efrat et al., 1993; Efrat et al., 1988; Hanahan, 1985; Knaack et al., 1994; Miyazaki et al., 1990). Such cell lines were useful for a better understanding of Beta cell biology and could be used for drug screening.

Generation of pancreatic Beta cells in large amount represents an important objective for at least 2 reasons: first such Beta cells would be useful for screening of new drugs that can modulate Beta cell function; next such pancreatic Beta cells could be used for cell therapy of diabetes. To this end, different approaches have been previously developed to generate pancreatic Beta cells in large amount.

The first one consisted in using as starting material immature stem cells (ES cells) to produce mouse or human Beta cells. The major advantage is that ES cells self-renew indefinitely in culture, and have the capacity to differentiate to multiple cell types, and thus to pancreatic Beta cells. While quite a large amount of publications appeared during the past years on Beta cells production from ES cells, (Assady et al., 2001; Blyszczuk et al., 2003; Brolen et al., 2005; Hori et al., 2002; Lumelsky et al., 2001; Soria et al., 2000), other publications described pitfalls in such works, questioned the interpretations and demonstrated that reproducible protocols were not yet available to produce Beta cells from ES cells (Hansson et al., 2004; Rajagopal et al., 2003).

Thus, at that point, functional Beta cells have not yet been generated in large quantities from ES cells with the exception of one recent publication where Beta cells developed from hES cells (D'Amour et al., 2006). However, such cells did not secrete insulin upon glucose stimulation.

The second approach was based on the production of pancreatic Beta cell lines using pancreas as a starting material. There, two main approaches have been followed. In the first case, adult Beta cells were transformed. This was performed either by x-ray induced rat insulinoma (Asfari et al., 1992; Gazdar et al., 1980), or by transformation of hamster islet cells by SV40 (Santerre et al., 1981) and more recently by immortalization of adult human Beta cells with SV40 LargeT antigen and human telomerase reverse transcriptase. While some cell lines were generated from adult Beta cells, the efficiency of the approach was extremely low. For example, while large efforts were developed to generate human Beta cell lines form adult islets (de la Tour et al., 2001; Demeterco et al., 2002; Gueli et al., 1987; Ju et al., 1998; Levine et al., 1995; Soldevila et al., 1991), only one human Beta cell line was developed (Narushima et al., 2005). The functional human Beta cell line NAKT-15 published in Narushima et al. represented a step toward a potential cure of diabetes by transplantation (Narushima et al., 2005). However, as indicated in this paper, among 253 clones analyzed, only one expressed insulin and transcription factors featuring Beta cells. This method is thus not amenable for obtaining large scale mature Beta cells for diagnosis or therapy.

Another approach was to derivate Beta cell lines from Beta cell tumours derived from transgenic mice expressing SV40 T antigen under the control of the insulin promoter (Efrat et al., 1995; Efrat et al., 1993; Efrat et al., 1988; Hanahan, 1985; Knaack et al., 1994; Miyazaki et al., 1990). However, because such Beta cell lines were obtained by gene transfer in fertilized eggs, its application is restricted to animal models without any possible transfer to human.

Recently, we demonstrated that immature pancreas infected with recombinant lentiviruses resulted in endocrine cell differentiation and restricted cell type expression of the transgene according to the specificity of the promoter used in the viral construct. Specifically, when eGFP was placed under the control of the insulin promoter, a majority of the developed Beta cells expressed eGFP. (Castaing et al., 2005b). Thus, recombinant lentiviral vectors can efficiently infect pancreatic progenitor cells and thereby stably modify mature rat pancreatic Beta cells. In addition, we asked whether Beta cell lines can be generated by infecting pancreatic progenitor cells that will differentiate into Beta cells. For this purpose, we infected immature rat or human pancreatic tissues with recombinant lentiviruses expressing SV40 largeT antigen and/or hTERT under the control of the insulin promoter. Our data demonstrate that recombinant lentiviruses can infect both rat and human pancreatic stem/progenitors, that will differentiate into Beta cells expressing the transgenes and form insulinoma from which Beta cell lines can be derived. For this purpose, rat immature pancreatic epithelia were transduced with recombinant lentiviruses expressing the SV40 LargeT antigen under the control of the insulin promoter. Such infected tissues were next transplanted under the kidney capsule of immuno-incompetent mice. Such environment had previously been shown to be permissive for the development of many organs such as ovarian cortex, thyroid, skin and airway (Delplanque et al., 2000; Levy et al., 1998; Martin et al., 1993; Weissman et al., 1999). We also demonstrated that pancreatic Beta cells also properly developed from rat or human immature pancreases under such conditions (Castaing et al., 2005a; Castaing et al., 2005b; Castaing et al., 2001).

In connection with the present invention, our objective was to define new approaches to generate functional Beta cell lines in sufficient quantity to provide cell therapy treatment.

We continued the investigations to maximize amplification of master cell batches of mature rat pancreatic Beta cells and we tried to apply the above method to generate master cell batches of human pancreatic Beta cells. Unfortunately, as of today, we never observed any formation of insulinoma with human cells contrary to what was observed when rat immature pancreases are infected with the same virus months after transplantation. Moreover, when we dissociated and cultured the infected cells, we were unable to generate human cell lines.

We also directly infected the cells with viruses expressing the hTert under the control of the insulin promoter together with recombinant lentiviruses expressing the SV40 LargeT antigen under the control of the insulin promoter and again, using conditions identical to the ones used to generate rat Beta cell lines, we were unable to generate human Beta cell lines.

We thus had to define a new strategy for gene transfer into Beta cell tumors to generate human Beta cell lines. In course of this work, we discovered that using a sub-graft protocol, we were able to form insulinoma-structure with human functional Beta cells and that the sub-grafting steps led to the specific enrichment in Beta cells ultimately leading to a homogenous human Beta cell lines which can be further amplified to clinical and commercial scale.

Accordingly, we now have at hand a method for specifically establishing and amplifying human Beta cells and not other cell types. By repeating enrichment and amplification steps, we were able obtain repeatedly cell lines which can be amplified for testing, diagnosis or therapeutic use.

Using the above sub-transplantation procedure to enrich the graft in proliferating beta cells, we were able to generate 11 independent human beta cell lines. Such lines express insulin and have a gene expression profile that resembles to adult beta cells. In addition, when transplanted under the kidney capsule of diabetic mice they were able to normalize blood glucose. the human beta cell lines are able to normalize glycemia of diabetic mice. By performing intraperitoneal glucose load these animals were able to utilize normally the glucose load, demonstrating their insulin secretion capabilities. Moreover, by performing glucose tolerance test in vivo on transplanted diabetic mice, we have been able to demonstrate that our cell line is able to respond to glucose stimulation and therefore is fully functional.

Finally, our human beta cell lines can be efficiently used to detect the presence of auto-antibodies found in sera of diabetic patients and thereby have a great potential for diagnosis of type I diabetes.

These Beta cells are now being used to generate and amplify ad infinitum human Beta cell lines which form master cell batches for diagnostic. This also opens perspective towards clinical use of Beta cells in the treatment of diabetes.

DESCRIPTION

Therefore, in a first embodiment, the invention is directed to a method of preparing Human pancreatic Beta cells or Human Beta cell tumors, comprising:

a) transducing and co-transducing immature human pancreases with i) a lentiviral vector expressing SV40 LargeT antigen under the control of the insulin promoter and ii) with a lentiviral vector expressing hTert under the control of the insulin promoter, or iii) a lentiviral vector expressing both SV40 LargeT antigen and hTert under the control of the insulin promoter, b) introducing the transduced immature pancreas obtained in a) into the kidney capsule of severe combined immunodeficiency (scid) animal, excepted human; c) allowing the transduced immature pancreas cells to develop insulinoma-like structures, wherein immature human pancreases cells in insulinoma-like structures have differentiated in insulin producing pancreatic Beta cells; d) micro-dissection of insulinoma-like structures obtained in step c), dissociation of cells thereof (and optionally transduction with a lentiviral vector expressing an antibiotic resistance gene under the control of the insulin promoter), e) sub-transplantation of the cells obtained in step d) into the kidney capsule of a new scid animal, excepted human, f) allowing the sub-transplanted cells in step e) to develop and regenerate insulinoma-like structures, wherein said newly developed insulinoma-like structures are enriched in insulin producing pancreatic Beta cells; g) micro-dissecting of insulinoma-like structures obtained in step f), dissociating and collecting the cells thereof, h) optionally, sub-transplantation of the cells obtained in step g) into the kidney capsule of a new scid animal, allowing further enrichment and amplification of insulin producing pancreatic Beta cells; optionally repeating step f), g) and h) until the appropriate amount of insulin producing pancreatic Beta cells is obtained.

The term "pancreatic cells" refers to cells obtained from the pancreas. In a preferred embodiment, the pancreatic function according to the invention is the regulation of glycemia and the correction of any metabolic anomalies due to destruction of Beta cells. The term "immature pancreatic cells" refers to cells which may be obtained from foetal pancreas or stem cells that have done a first differentiation in endodermic cells.

The scid non human animal as referred herein can be non obese diabetic/severe combined immunodeficiency (NOD/scid) animal is selected among bovines, porcines, horses, sheep, goats, primates excepted humans, rodents such as mice, rats, hamsters. In a preferred embodiment, the NOD/scid animal is a mouse. Preferably the NOD/scid mice of the invention are of any age of development, preferably sufficiently old to perform a graft into the kidney capsule. Preferably, the NOD/scid mice are about of the 2 to 15 weeks of development, more preferably to 6 to 8 weeks of development. A NOD/scid animal is an animal lacking T and B lymphocytes and failing to generate either humoral or cell mediated immunity.

Antibiotic resistance gene is selected in the group consisting of hygromycin resistance gene, neomycin resistance genes, tetracyclin resistance gene, ampicillin resistance gene, kanamycin resistance gene, phleomycin resistance gene, bleomycin resistance gene, geneticin resistance gene, carbenicillin resistance gene, chloramphenicol resistance gene, puromycin resistance gene, blasticidin-S-deaminase gene. In a preferred embodiment, said antibiotic resistance gene is a neomycin resistance gene. In this case, the selective agent is G418.

The above method includes collecting the human functional pancreatic Beta cells obtained at step h) which form an homogenous cell population. The cell population can further be cultured in vitro to establish a human functional Beta cell line. At this stage, the cells derived from the successive sub-grafts contained the SV40 LargeT, the hTERT and the antibiotic resistance transgenes. Thus, the cell lines obtainable by the above method are immortalized and depending on the end point they may or may not be reversed (de-immortalized).

The above method to prepare human functional pancreatic Beta cells is particularly useful for testing and screening candidate medicament for treating diabetes in vivo after graft in non human animals, such as mice or rats, or in vitro.

In this regard, and in one specific embodiment, the above method can be practiced to prepare large amount of human functional pancreatic Beta cells for testing and screening purposes as well as for in vitro diagnosis allowing classification of patients in type 1 or 2 diabetes. Here, the cells may be de-immortalized. On the contrary, with the above method, one can repeat steps f) g) and h) as necessary to provide large amount of insulinoma or isolated human Beta cells thereof and these cells may further be amplified in culture in vitro ad infinitum. Cross section of Beta cell tumors, cells derived thereof or protein extract from these cells can be bond or adsorbed to a solid support (for example polylysine coated plates) and reacted with the plasma serum of individuals. After incubation, the serum is washed out and the presence or absence of autoantibodies against different surface antigens specific to autoimmunity associated with diabetes is revealed (for example by means of labeled anti-human Ig).

Therefore, the invention is aimed at the Human Beta cell tumors or insulinomas or human pancreatic Beta cells obtainable by the above method. Human Beta cell tumors or Human pancreatic Beta cells display at least one of the following features:

Carboxypeptidase-A negative transcriptional factor Pdx1 positive transcription factor MafA positive proconvertase Pcsk1 positive expression of Glucose transporter Glut2 expression of Kcnj11 and Abcc8 coding for subunits of the potassium channel expression of zinc transporter Znt8 (Slc30a8)

expression of insulin

Human Beta cell tumors or human pancreatic Beta cells as defined above are also positive to reaction with anti-insulin, anti-GAD and/or anti-IA2 antibodies and can be maintained and grown in culture in a medium free of serum and on Matrigel and fibronectin coated wells. Thus, the invention also contemplates a cell culture comprising the above Human pancreatic Beta cells in culture in a medium free of serum comprising Matrigel and fibronectin. This cell culture allows to expand and to establish immortalized Human pancreatic Beta cell lines.

In addition, the invention relates to a method of in vitro diagnosis diabetes comprising reacting section of Beta cell tumors, cells derived thereof or protein extract of these cells obtainable by the method depicted above with the plasma serum of individuals, detecting the presence or absence of autoantibodies against different surface antigen specific to type 1 or type 2 diabetes, such as Islet Cells Antibodies (ICA), or more specific antibodies recently identified like antibodies against Insulin autoantibodies (IAA) and glutamic acid decarboxylase antibodies (GADA) or IA-2 antibodies (IA2A) or specific unknown antibodies. The identification of known or new antibodies can be performed by immunoblot or dot-blot for example.

This aspect of the invention provides for the first time a kit that can be prepared at a commercial scale for diabetes classification. More particularly, specific autoantibodies are Islet Cells Antibodies (ICA) selected from Insulin autoantibodies (IAA) and glutamic acid decarboxylase antibodies (GADA). Indeed, these antigen are expressed at the surface of the Beta cell tumors or cells derived thereof obtainable according to the above method. Thus, embraced herein is a diagnostic kit for diabetes comprising Beta cell tumors or human functional pancreatic Beta cells obtainable by the above method, or proteins extract there from, optionally bond or adsorbed to a solid support.

In another embodiment, the cells as described above are cultured in vitro and pancreatic Beta cell lines are established for screening compounds capable of modulating insulin secretion.

In still another embodiment, the above method is directed to the establishment of master cell banks for cell therapy of diabetes. Here, the method further includes steps for de-immortalization of the cells. In another words, the Lentivirus vectors above are constructed to allow reversible or conditional immortalization. In this regard, in the lentiviral vectors expressing the SV40 LargeT, the hTERT and the antibiotic resistance transgenes under the insulin promoter control, at least one Lox P site is introduced. Preferably, the vectors according to the invention are constructed so that the SV40 LargeT and the hTERT transgenes are within two Lox P site. Said transgenes are removed by expressing the Cre recombinase in the Beta cells. For example the cells obtainable by the above method are transduced by a vector or plasmid expressing a Cre recombinase and reversion occurs. Of course, the skilled in the art may choose to use the FRT/FLP system to remove said transgenes. Methods for reverting immortalized cells are described in WO 01/38548.

In a particular embodiment, the lentiviral vector expressing SV40 LargeT and the lentiviral vector expressing hTERT further comprise a LoxP or a FRT site, provided that site specific recombination sites are different in both vectors.

Negative selection step can also be performed after the action of the Cre or FLP recombinase. This further step allows selecting only the cells in which the immortalization genes SV40 LargeT and hTERT, as well as the antibiotic resistance gene, have been removed. These cells can be frozen, stored and optionally encapsulated, until they are transplanted into diabetic patients.

Thus, lentiviral vectors may also include at least one negative selection marker gene. For example, the genes encoding for such proteins are the HSV-TK gene; in that case the selective agent is Acyclovir-Gancyclovir. For example, the genes encoding for such proteins are the Hypoxanthine phosphoribosyl transferase (HPRT) gene or the guanine-phosphoribosyl-transferase (Gpt) gene; in these cases, the selective agent is the 6-Thioguanine. For example, the gene encoding for such proteins is the cytosine deaminase; in that case the selective agent is the 5-fluoro-cytosine. Other examples of negative selection marker proteins are the viral and bacterial toxins such as the diphteric toxin A (DTA).

In still another embodiment, the invention relates to the Beta cell tumors and isolated cells thereof obtainable by the above method. As explained, both immortalized and de-immortalized are encompassed herein.

The invention also concerns the use of said cells for testing or screening candidate medicaments for the treatment of diabetes, for in vitro diagnosis as explained above and for cell therapy of diabetes.

The present invention also provides a method of regenerating pancreas function in an individual afflicted with diabetes, the method comprising transplantation of an effective amount of the human functional pancreatic cells as defined above, said cells being reverted to a primary Beta cell phenotype, into said individual.

The invention also relates to a pharmaceutical composition comprising an effective amount of the human functional pancreatic cells as defined above, said cells being optionally encapsulated.

An "effective amount" is an amount sufficient to effect beneficial or desired clinical results. An effective amount, for example from $10^5$ to $10^9$ cells, can be administered in one or more applications, although it is preferable that one administration will suffice. For purposes of this invention, an effective amount of stem cells precursors of pancreatic Beta cells is an amount that is sufficient to produce differentiated pancreatic cells which are able to restore one or more of the functions of the pancreas. It is contemplated that a restoration can occur quickly by the introduction of relatively large numbers of pancreas cells, for example greater than $10^9$ cells. In addition, it is also contemplated that when fewer pancreatic cells are introduced, function will be restored when the pancreas cell or cells are allowed to proliferate in vivo. Thus, an "effective amount" of pancreatic cells can be obtained by allowing as few as one pancreas cell sufficient time to regenerate all or part of a pancreas. Preferably, an effective amount administered to the individual is greater than about $10^1$ pancreas cells, preferably between about $10^2$ and about $10^{15}$ pancreas cells and even more preferably, between about $10^3$ and about $10^{12}$ pancreas cells. In terms of treatment, an "effective amount" of pancreatic cells is the amount which is able to ameliorate, palliate, stabilize, reverse, slow or delay the progression of pancreas disease, such as diabetics.

Methods of introducing cells into individuals are well known to those of skill in the art and include, but are not limited to, injection, intravenous or parenteral administration. Single, multiple, continuous or intermittent administration can be effected. The pancreas cells can be introduced into any of several different sites, including but not limited to the pancreas, the abdominal cavity, the kidney, the liver, the celiac artery, the portal vein or the spleen. Preferably, the pancreas cells are deposited in the pancreas of the individual.

It is another embodiment of the present invention to provide pancreatic cells of the invention as a medicament. More precisely, the present invention relates to the use of pancreatic cells of the invention for preparing a medicament to treat diabetics, hypoglycemia, or pathologies associated to a dysfunction of the digestive enzymes, especially individual with insulin-dependent diabetes (T1D).

FIGURE LEGENDS

FIG. 1: Development of the infected tissue after transplantation

Pancreatic epithelia were infected with pTrip ΔU3.RIP405-eGFP (A) or pTRIP ΔU3.RIP405-SV40 largeT (B, C), transplanted and analyzed one month after (A, B) or three months after C. The developed transplanted tissue is cycled with a dashed line. Insulin detection by situ hybridization (blue) on 10 μm sections on grafts removed one month after transplantation. Grafts were infected with pTrip ΔU3.RIP405-eGFP (D, E) or pTRIP ΔU3.RIP405-SV40 largeT (F, G). E, G: Double staining for insulin (blue) and BrdU (brown)

Scale bars: A-C 2 mm; D, F 1 mm; E, G 25 μm.

Figure 2:
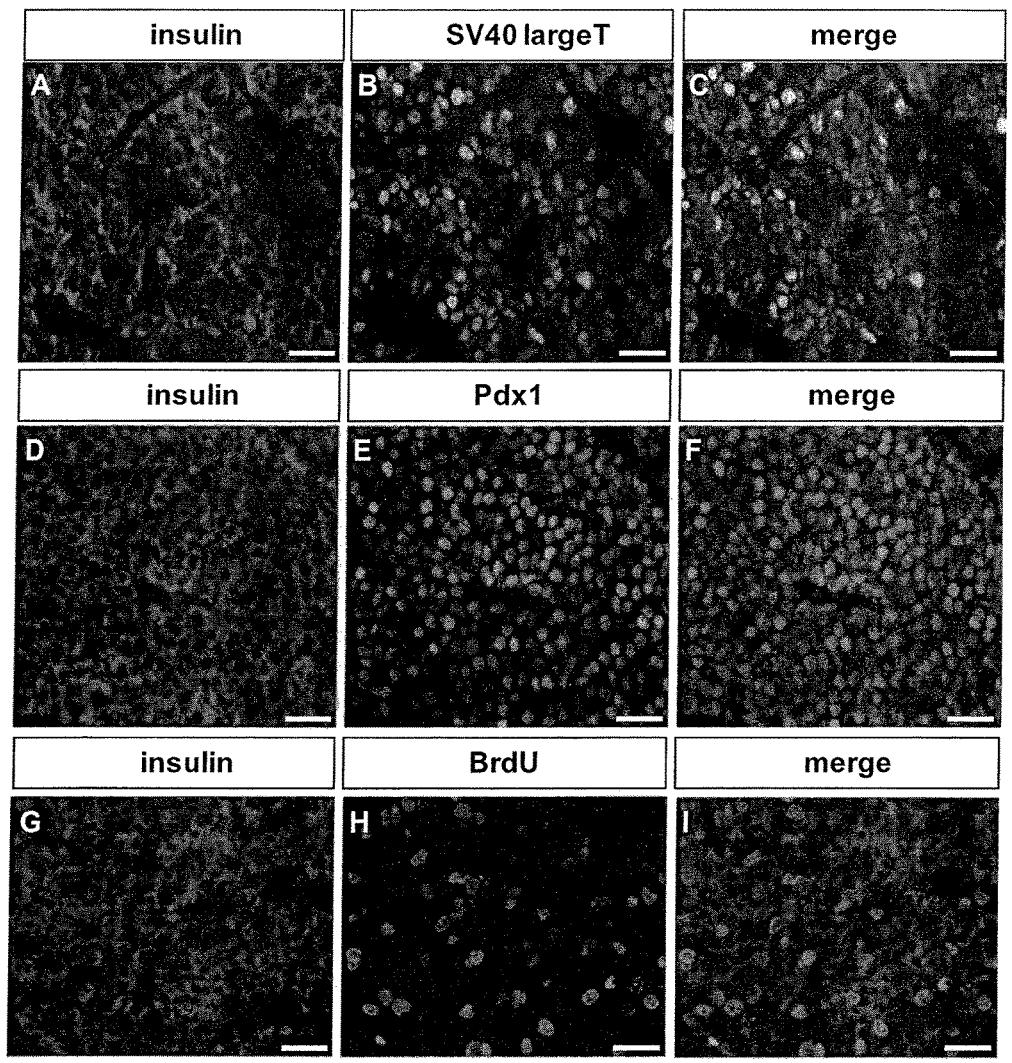

FIG. 2: Immunohistochemical analysis of grafts developed in Scid mice.

A-I represent sections through the graft, while J-L represent sections through the kidney.

A-C: Double staining for insulin (red) and SV40 largeT (green); D-F: Double staining for insulin (red) and Pdx1 (green); G-I: Double staining for insulin (red) and BrdU (green);

Scale bars: 25 μm

Figure 3:
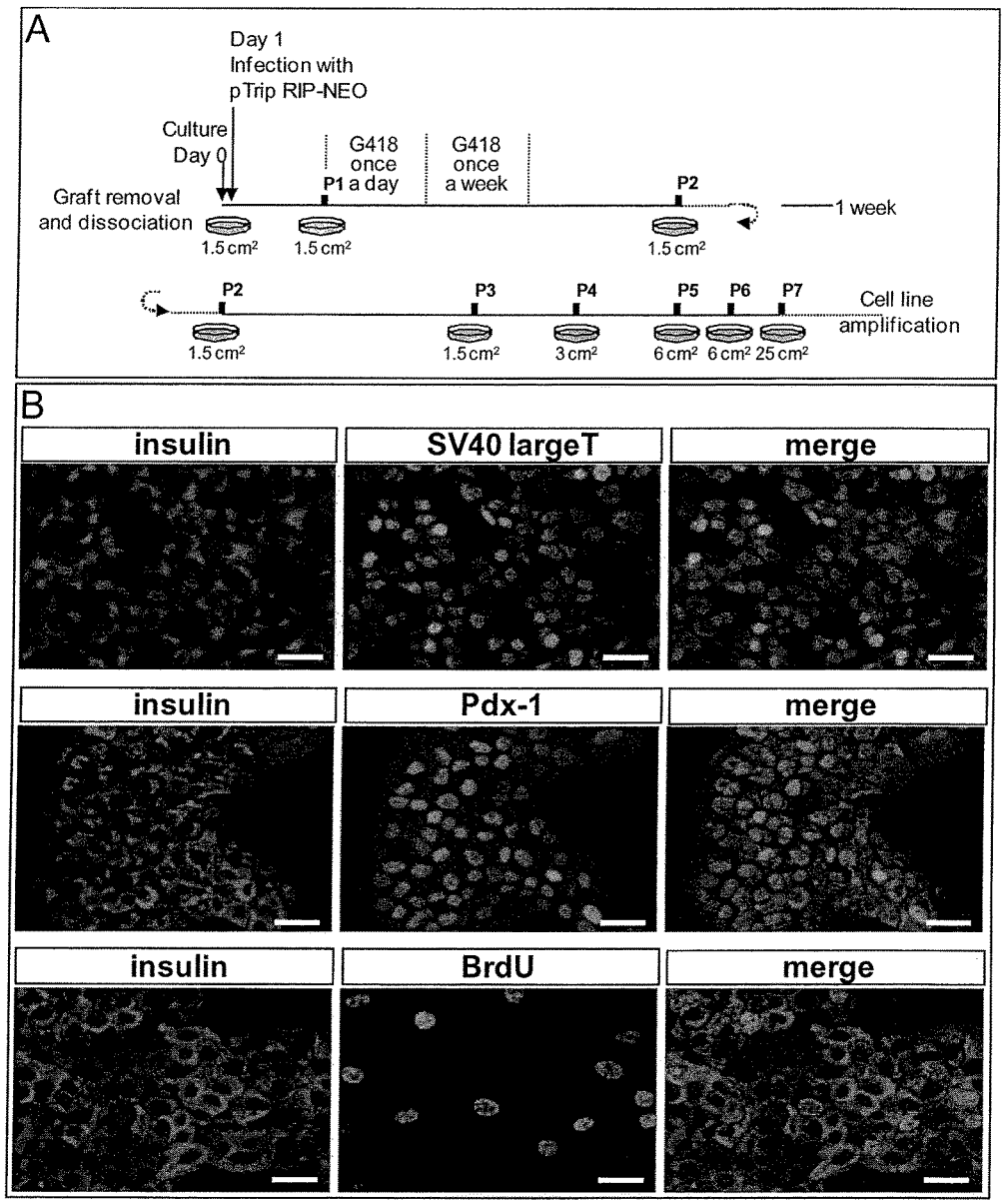

FIG. 3: establishment of the RYAS41 cell line that coexpress insulin, SV40LT and Pdx1 and proliferate.

A: Schematic representation of the culture procedure used to derive the RYAS41 cell line. P represents the passage number. Surface of the culture well is indicated below the time line.

B: Top panel: coexpression of insulin (red) and SV40 largeT (green). Middle panel: coexpression of insulin (red) and Pdx1 (green). Bottom panel: Insulin-positive cells (red) incorporate BrdU (green) after a 2 hour pulse.

Scale bars: 25 μm

Figure 4:
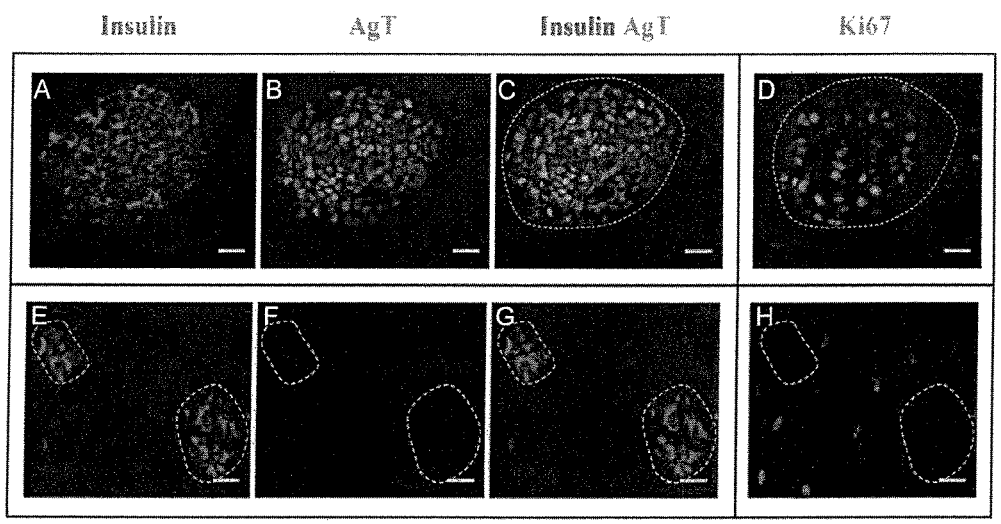

FIG. 4: Proliferating Beta cells are observed after infection of human fetal pancreas with SV40 LT Sections through the graft 6 months after transplantation and infection with pTrip ΔU3. RIP SV40 LT lentiviral vector. Large islet-like structures expressing SV40LT and insulin are observed in the graft (A-C) and contained proliferating Beta cells expressing Ki67 (D). The smaller islet-like structure in the graft (E-H) expressed insulin (E, G) and stained negative for SV40 LT (F, G) and Ki67 (H).

Figure 5:
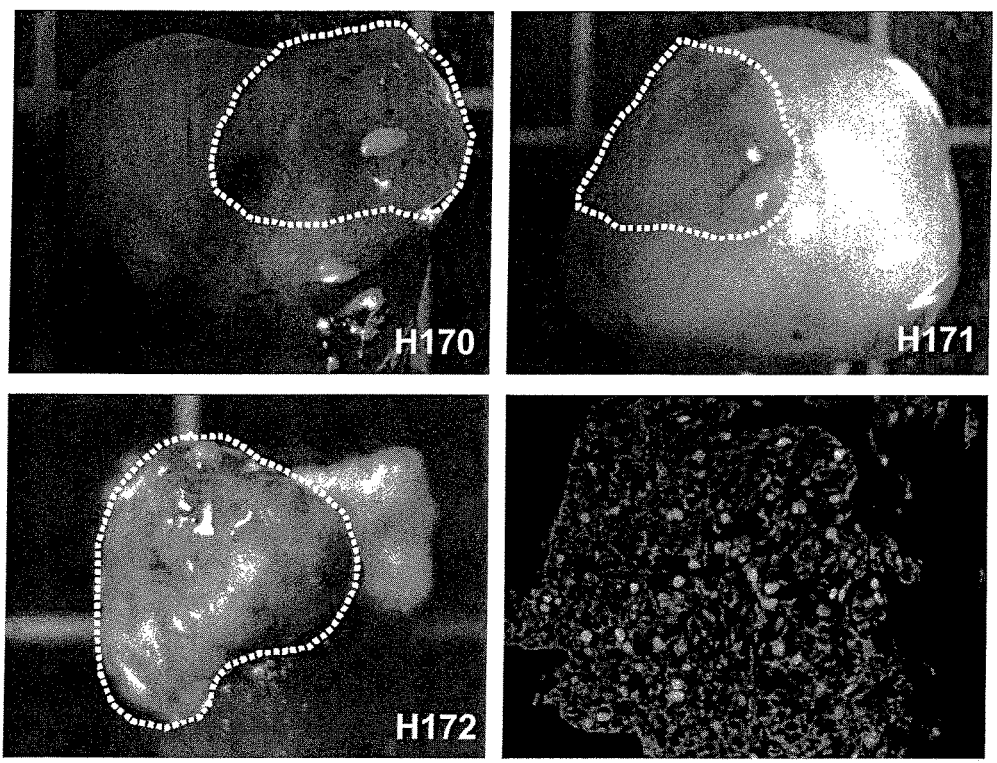

FIG. 5: 10 to 12 months after transplantation insulinoma like regions are found in the graft Photographs of three independent grafts infected with SV40 LT expressing lentiviral vector. Grafts were removed either 10 months (HYAS 170, HYAS 171) or 12 months (HYAS 172) after transplantation. Dotted line focuses on highly vascularized region of the graft. Such regions were sectioned and analyzed by dual immuno fluorescent detection of both insulin (red) and Ki67 (green).

Figure 6:
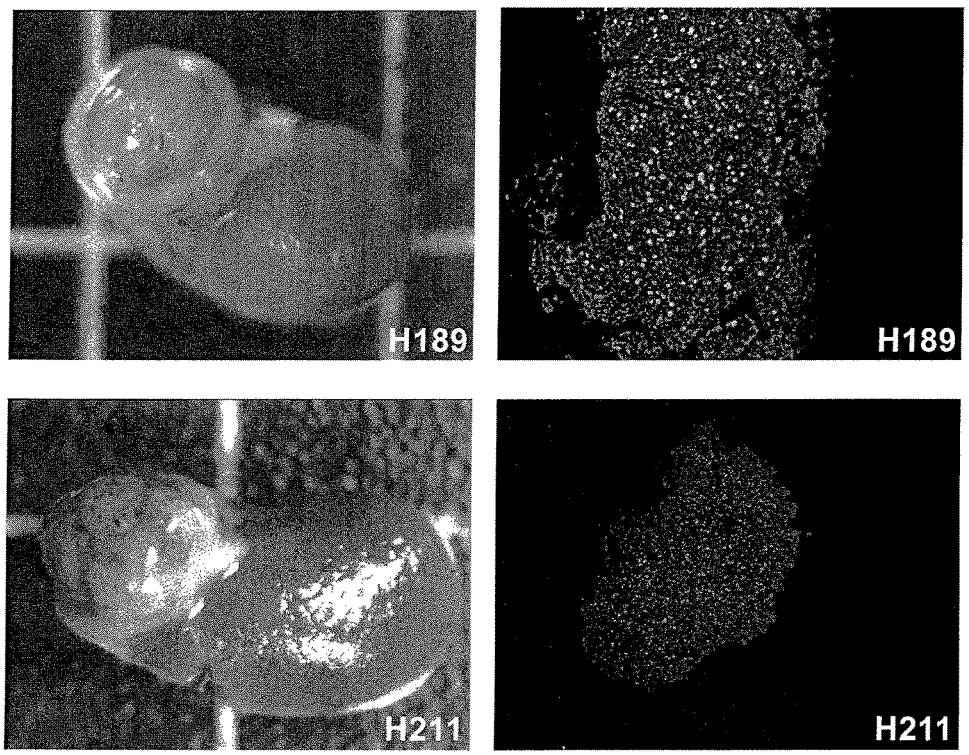

FIG. 6: Sub transplanted tissue re-infected with hTERT expressing lentiviral vector are composed of homogeneous insulin expressing cells that proliferate.

Examples of two sub transplanted tissue re infected with a lentiviral vector expressing hTERT. Both cHYAS 189 and cHYAS 211 were removed 6 months after sub transplantation. Sections trough these grafts indicate an homogeneous insulin expression (red) and active proliferation as observed with Ki67 expression (green).

Figure 7:
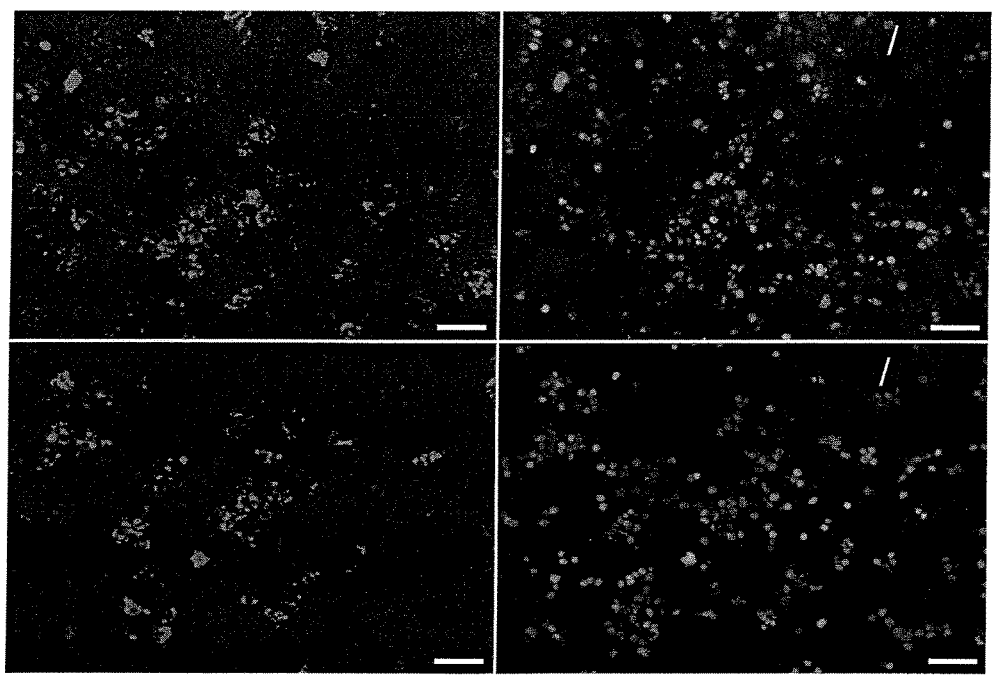

FIG. 7: The Beta cell line proliferates and expresses in culture insulin and pdx1

Co-immuno staining in culture well for insulin (red) and either Ki67 proliferation marker (green top panel) or pdx1 (green bottom panel)

Scale bars: 50 μm

Figure 8:
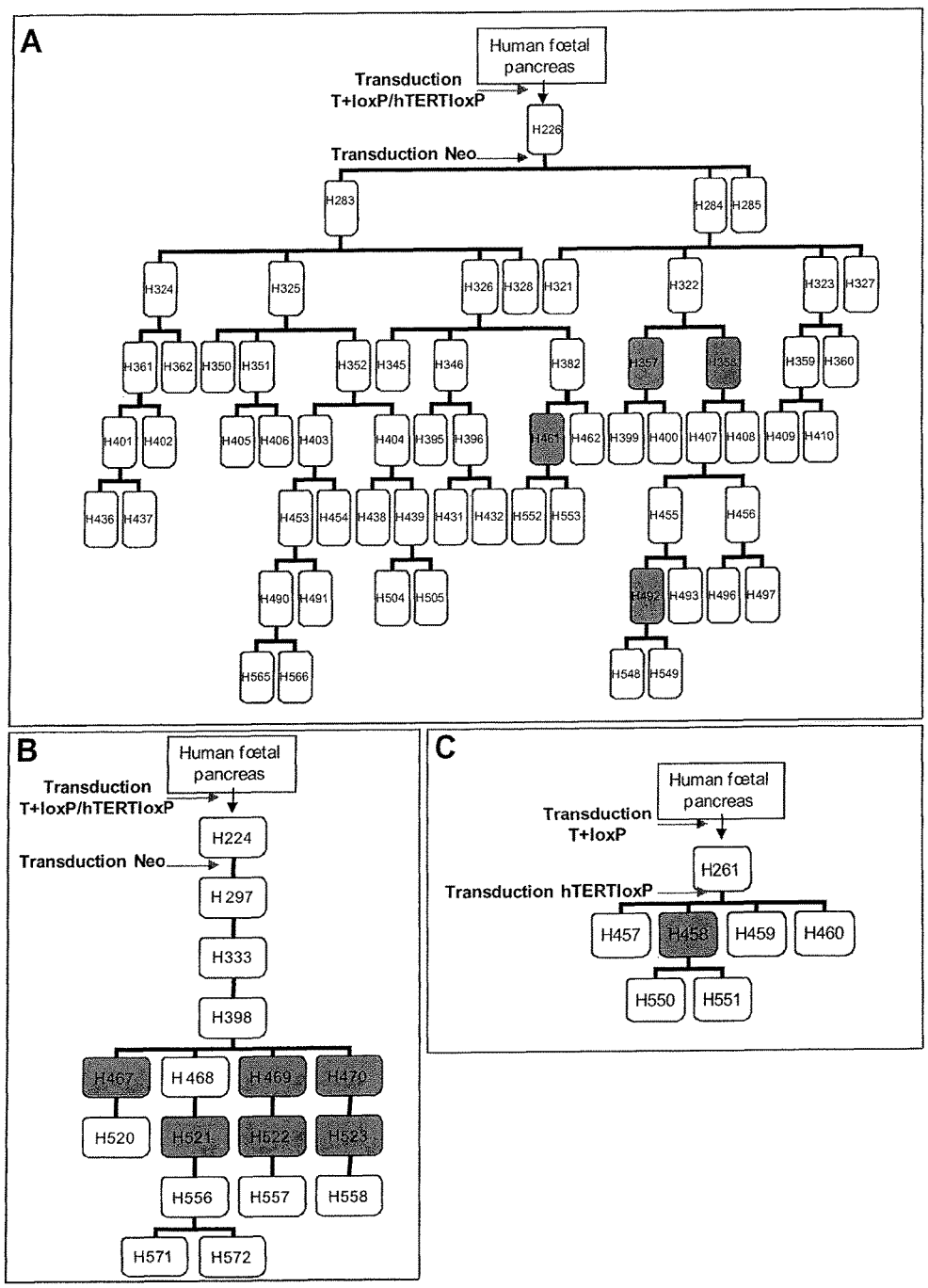

FIG. 8: Genealogy of all derived human beta cell lines 11 independent human Beta cell line have been derived (red box) originating from 3 different fetal human pancreases A=H226; B=H224 C=H261. The genealogy of all successive sub-transplantation is summarized FIG. 9: Comparative expression of insulin, IAPP and pdx1 in 6 independent human beta cell lines Quantitative RT-PCR was performed to compare expression of insulin (A), IAPP (B) and pdx1 (C) in 6 independent human Beta cell lines that are representative of the 3 initial fetal human pancreases that were used to derive these cell lines. Values are fold expression compared to human adult islets.

Figure 10:
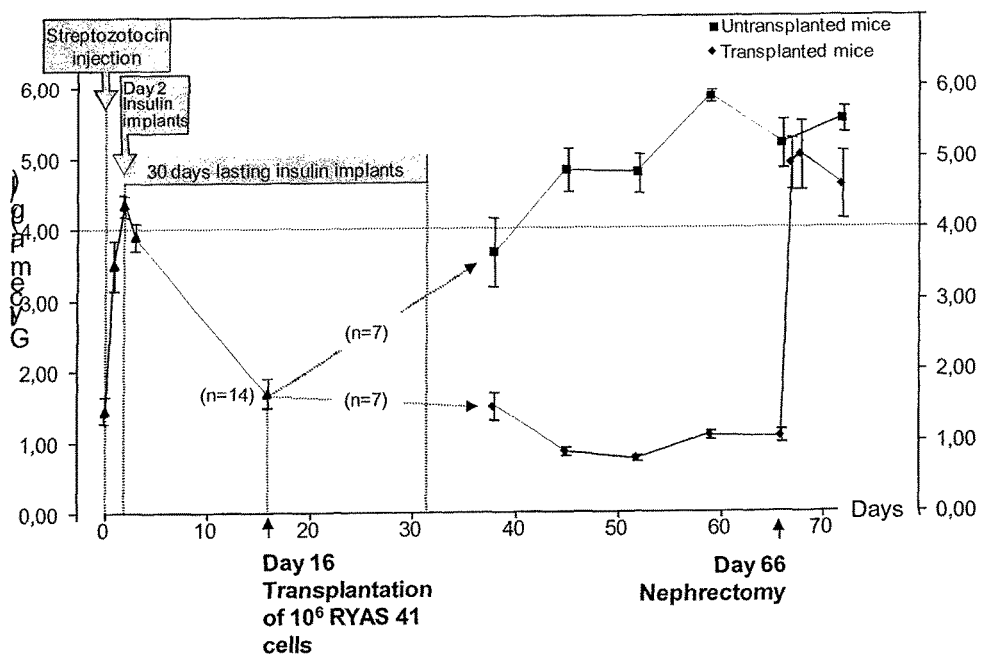

FIG. 10: Transplanted RYAS41 cells can restore normoglycemia in diabetic mice scid mice were injected with streptozotocin. Two days after injection the mice were hyperglycemic and insulin capsules were subcutaneously implanted. 16 days after STZ injection $10^6$ RYAS41 cells were transplanted under the kidney capsule. Once it was observed that the insulin implants had no more effect the glycemia of the transplanted mice remained stable while the untransplanted ones displayed clear hyper glycemia. When grafts were removed by nephrectomy at day 66 glycemia increased rapidly. Values are means (n=14 or 7)+/−S.E.M.

Figure 11:
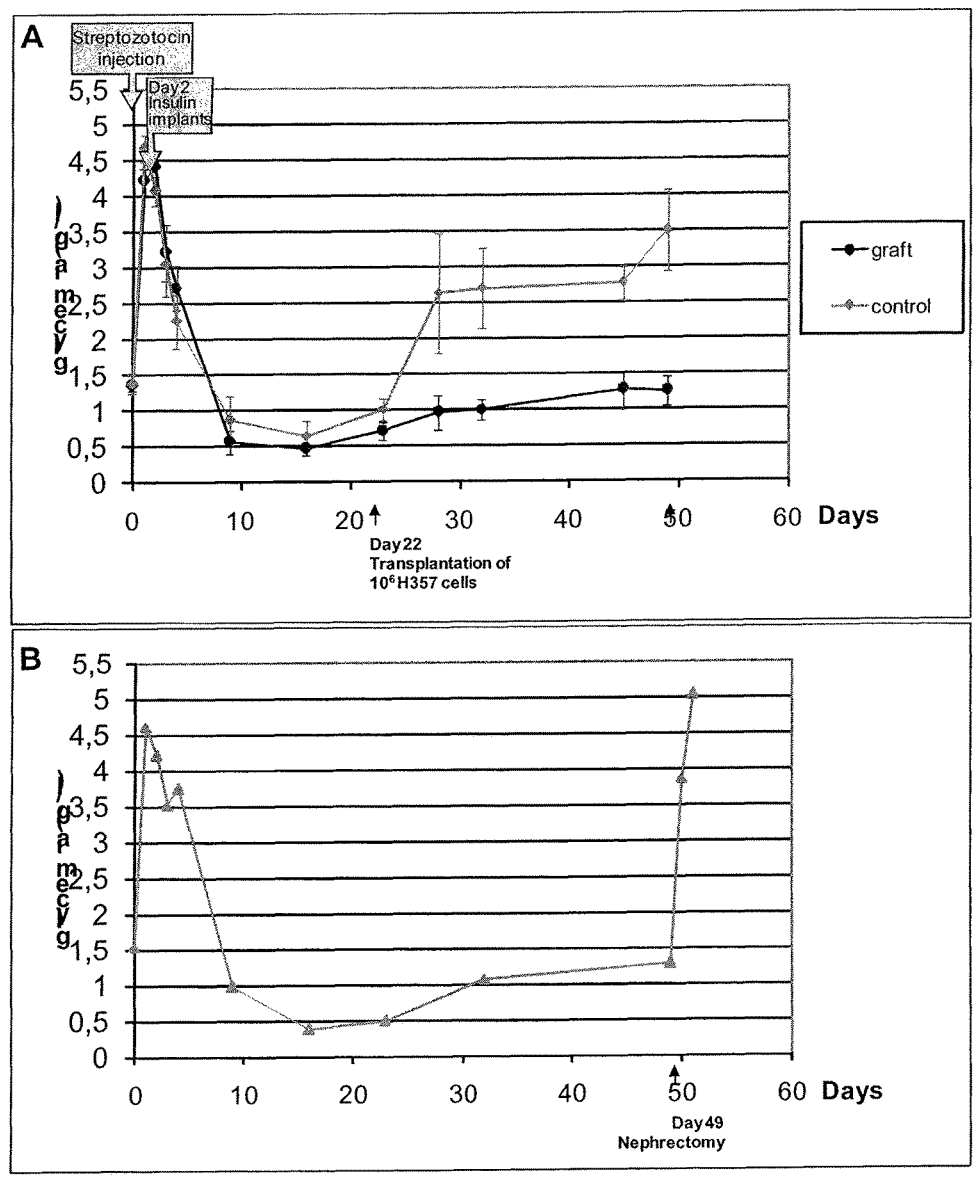

FIG. 11: Transplanted H357 human Beta cell line cells can restore normoglycemia in diabetic mice scid mice were injected with streptozotocin. Two days after injection the mice were hyperglycemic and insulin capsules were subcutaneously implanted. 22 days after STZ injection 10⁶ H357 human Beta cell line were transplanted under the kidney capsule. Once it was observed that the insulin implants had no more effect the glycemia of the transplanted mice remained stable while the untransplanted ones displayed clear hyper glycemia. B: When the graft was removed by nephrectomy on one of the transplanted mouse at day 49 glycemia increased rapidly.

Values are means (n=10 for transplanted mice and n=4 for controls)+/−S.E.M.

Figure 12:
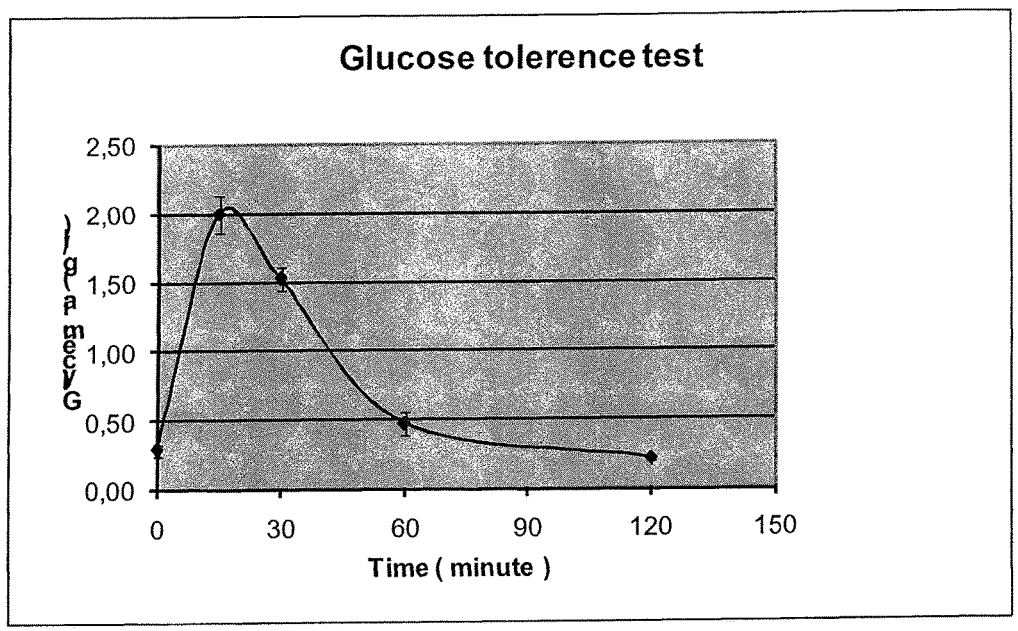

FIG. 12: Glucose tolerance test 16 hours fasting diabetic transplanted mice were injected with glucose (2 mg/G of body weight) and glycemia was monitored over a 2 hours period. Values are means (n=3)+/−S.E.M.

Figure 13:
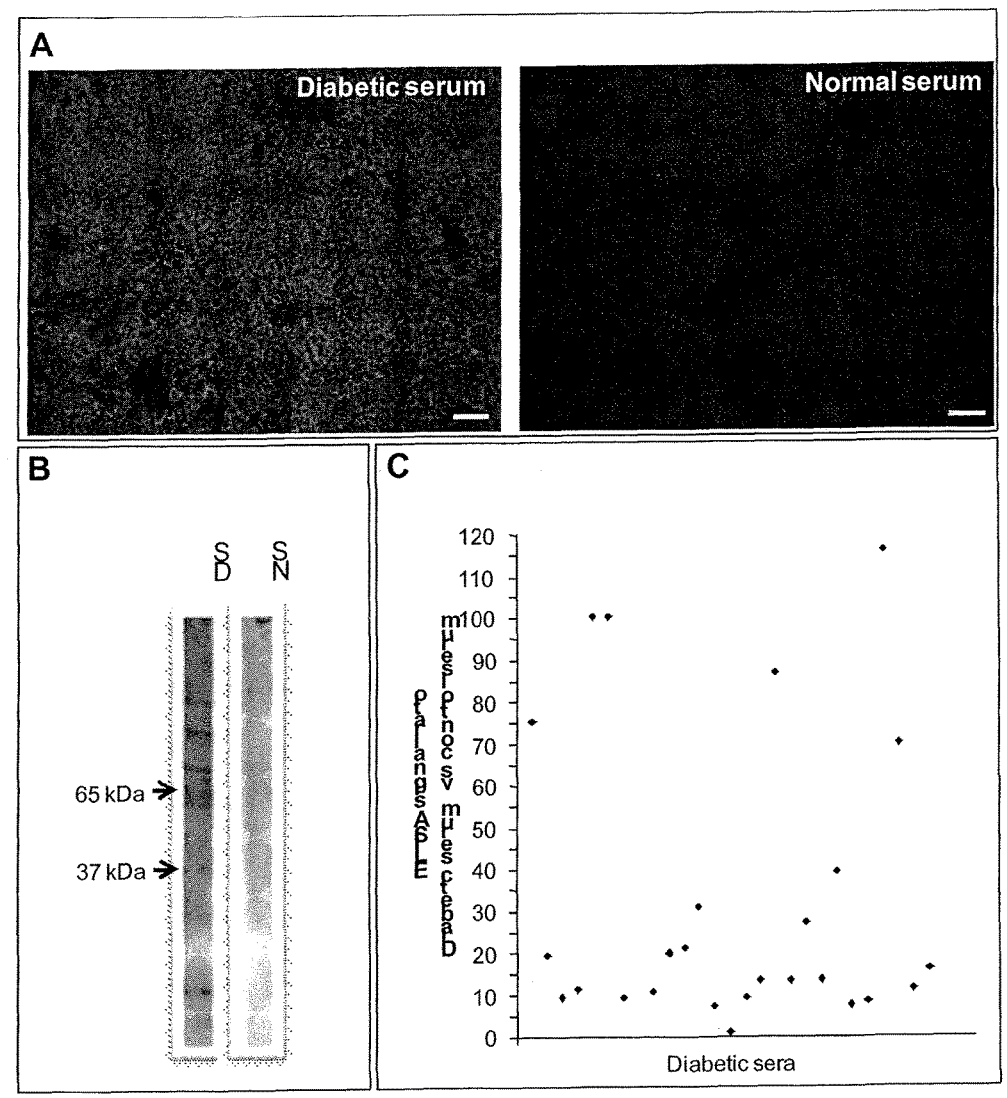

FIG. 13: Tumoral tissue that developed in scid mice can be use to detect auto-antibodies present in sera of diabetic patients.

A: Frozen unfixed section of the H212 human graft can detect by indirect immune-fluorescence auto-antibodies present in the serum of diabetic patient (left panel) when compared to control serum (right panel).

B: Specific protein can be visualized on western blot of H301 protein extracts with the serum of a diabetic patient whereas no specific proteins are detected with control serum. Specific bands with molecular weight corresponding to GAD (65 kDa) and IA2 (37 kDa) are indicated with an arrow.

C: ELISA test prepared with protein extracts from graft H301 allows efficient detection of 25 out of 26 sera from diabetic patients.

GENERAL MATERIALS AND METHODS

DNA Constructs and Recombinant Lentiviral Productions

The backbone of the lentiviral construct, pTRIP, has been previously described (Zennou et al., 2000). The lentiviral vector, pTRIP ΔU3.RIP405-eGFP expresses eGFP under the control of the Rat insulin II gene promoter (RIP) (Castaing et al., 2005b). New lentiviral vectors pTRIP ΔU3.RIP405-LargeT and pTRIP ΔU3.RIP405-NEO were constructed in order to express, under the control of the insulin promoter, the SV40 largeT antigen or the neomycin resistance gene respectively. First the eGFP cassette was removed from pTRIP ΔU3.RIP405-eGFP by BamH1 and Kpn1 restriction. The following linker, GATCGCCCCGGGCGGGATCCGG-TAC (SEQ ID NO: 1) with BamHI and KpnI cohesive ends was ligated to the linearized plasmid resulting in the pTRIP ΔU3.RIP405-linker containing downstream of the insulin promoter Sma1, BamHI and KpnI unique cloning sites in the 5' to 3' orientation. A BamHI insert containing the entire coding region of the SV40 large T antigen (kindly provided by B. Thorens) was ligated to a BamHI linearized pTRIP ΔU3.RIP405-linker. The complete coding region of the neomycin resistance gene was amplified from the pcDNA 3 plasmid (Invitrogen) by PCR using the following primers: BamH1-Neo sense: 5' gaggaggatccCGCATGATT-GAACAAGATGG 3' (SEQ ID NO: 2) and KpnI-Neo antisens 5' cccaaggtaccCGCTCAGAAGAACTCGTCAAG 3' (SEQ ID NO: 3). The resulting PCR product was digested with both BamH1 and Kpn1 and ligated in a BamH1, Kpn1 linearized pTRIP ΔU3.RIP405-linker. To rule out PCR induced mutations the neomycin resistance coding region was entirely sequenced. A new lentiviral vector pTrip ΔU3.RIP405 hTERT expressing the human Telomerase reverse transcriptase (hTERT) under the control of the rat insulin promoter (RIP) was constructed. First the RIP 405 bp fragment was purified from a Mlu1 BamH1 digestion of the pTRIP ΔU3.RIP405-eGFP and inserted in an empty pTrip vector containing a Mlu1, BamH1 and Xbo1 polylinker. The resulting vector was linearized with Xha1 and used to clone a 3497 bp Xba1 fragment containing the complete hTERT coding sequence previously purified from digestion of SIN-PGK hTERT vector (kindly provided by B. Thorens). Lentiviral vector stocks were produced by transient transfection of 293T cells with the p8.7 encapsidation plasmid (ΔVprΔVifΔVpuΔNef) (Zufferey et al., 1997), pHCMV-G encoding the VSV glycoprotein-G and the pTRIP ΔU3, recombinant vector as previously described (Zennouo et al., 2000). The supernatants were treated with DNAse I (Roche Diagnostic) prior to ultracentrifugation and the resulting pellet was resuspended in PBS, aliquotted and frozen at −80° C. until use. The amount of p24 capsid protein was quantified by the HIV-1 p24 ELISA antigen assay (Beckman Coulter). All infections were normalized relative to p24 capsid protein quantification.

Preparation of Rat Pancreatic Rudiments

Pregnant Wistar rats were obtained from Janvier (CERJ, Le Genest, France). All animal manipulations were performed according to the guidelines of the French Animal Care Committee. The morning post coitum was designated as embryonic day 0.5 (E0.5). Pregnant female rats at E13.5 days of gestation were sacrificed by cervical dislocation.

The embryos were harvested on E13.5 and dissected. The dorsal pancreatic bud was dissected as described previously (Duvillie et al., 2003; Miralles et al., 1998). Briefly, the stomach, pancreas, and a small portion of the intestine were dissected together; then the mesenchyme was separated from the pancreatic epithelium as follows: the digestive tract was incubated with 0.5 mg/ml collagenase A (Roche, France) at 37° C. for 30 minutes then washed several times with Hank's balanced salt solution (HBSS, Invitrogen, France) at 4° C., and the epithelium was mechanically separated from the surrounding mesenchyme using needles on 0.25% agar, 25% HBSS, 75% RPMI (Gibco) gel in a Petri dish.

Preparation of Human Pancreatic Rudiments

Human pancreases were extracted from fetal tissue fragments obtained immediately after elective termination of pregnancy performed by aspiration between 8 and 10 weeks of development, in compliance with French legislation and the guidelines of our institution. Warm ischemia lasted less than 30 minutes. Gestational ages were determined on the basis of time since the last menstrual period, crown-rump length measured by ultrasonography, and hand and foot morphology.

Human fetal pancreases were treated in 0.5 mg/ml collagenase A (Roche) in RPMI (Gibco) at 37° C. Treatment duration depends on the age of the fetus: 15 min for an 8 week old pancreas and 25 min for a 12 week old pancreas. The tissue was then rinsed few times in ice cold 1×HBSS (Gibco) and then transferred on a petri dish containing 0.4% agar prepared in RPMI. The head and the tail of the pancreas were separated with a 30 gauge needle and mesenchymal cells were partially removed generating human pancreatic epithelium partially depleted from its surrounding mesenchyme.

Infection of Rat Immature Pancreases.

Recombinant lentiviruses were used to infect rat immature pancreatic epithelia. 1 μg of p24 of either pTrip ΔU3.RIP405-eGFP or pTRIP ΔU3.RIP405-largeT was preincubated in a final volume of 45 μl of RPMI 1640 medium supplemented with 10% heat inactivated fetal calf serum containing HEPES (10 mM), L-glutamine (2 mM), non essential amino acid (Invitrogen) and penicillin (100 units/ml)-streptomycin (100 µg/ml). To increase the viral infection efficiency, DEAE-dextran was added to the culture medium to a final concentration of 20 µg/ml. After 15 min at 37° C. of pre-incubation the viral solution was added to 45 µl of Hepes Buffered Saline Solution (HBSS, Invitrogen) containing 10 pancreatic epithelia. After 2 hours of infection tissues were washed twice in culture medium. and grown overnight in three-dimensional collagen gels as described previously (Miralles et al., 1998). The following day, the epithelia were removed from the collagen matrix and used for transplantation into severe compromised immunodeficient (scid) mice as described (Castaing et al., 2005b).

Infection of Human Immature Pancreas

The partially depleted human pancreas was infected in a minimal volume of 200 µl for 1 hour at 37° C. with an amount of virus corresponding to 2 µg of p24 protein. The composition of the infection medium is as follow: RPMI medium (Gibco) supplemented with 10% heat-inactivated fetal calf serum (FCS), 1% non-essential amino-acids (Gibco), 1% P/S (Gibco) and DEAE dextran at 10 µg/ml. Infection medium is pre-incubated 15 minutes at 37° C. with the virus before being added to the pancreatic explants. At the end of infection, 800 µl of virus-free medium is added to the explants and let over-night at 37° C. The following day, the explants are transplanted under the kidney capsule of a scid mice (Castaing et al., 2005b; Castaing et al., 2001).

Transplantation of Infected Tissues

Male scid mice (Charles River Laboratories, L'arbresle, France) were maintained in isolators.

Using a dissecting microscope, ten infected rat pancreatic epithelia or partially depleted human pancreas were implanted under the kidney capsule as previously described (Castaing et al., 2005b; Castaing et al., 2001), with the following modifications. The left kidney was exteriorized; a small transverse incision was made through the capsule on the ventral surface of the kidney, near the inferior pole. A small silicon cylinder was pushed under the capsule to provide a sealed space to confine the transplanted cells and tissues (Thomas et al., 1997). The tissues were then introduced into the cylinder using forceps and/or a Hamilton syringe. At different time points after transplantation, the mice were sacrificed, the kidney removed, and the graft dissected. Tissues were used for different purposes: (i) fixed and used for immunohistological analysis or for in situ hybridization; (ii) dissociated and either used to establish Beta cell lines or sub-transplanted to new scid mice. Some mice were pulsed with BrdU (Sigma-Aldrich) 2 hour before sacrifice for cell proliferation analysis.

Graft Dissociation of Rat Transplanted Tissues.

Three month after transplantation the scid mice were sacrificed by cervical dislocation and the graft was removed in a sterile cabinet and weighted. The graft was then cut into 50 mg pieces. Using micro-scissors, each piece of tissue was independently cut as fine as possible and treated with 200 units of type IV collagenase (Worthington) in 500 µl of HBSS during 20 min at 37° C. The digested tissue was next pooled and centrifuged for 10 min at 2000 rpm. The resulting pellet was resuspended in culture medium containing DMEM (Invitrogen), 15% heat inactivated fetal calf serum, 0.5% 2-mercaptoethanol (Merck) and penicillin (100 units/ml)-streptomycin (100 µg/ml). The suspension was mechanically dissociated in a 1 ml syringe by successive passages through 21, 22, 25, 27 and 30 gauge needles. The dissociated cells were centrifuged 10 min at 2000 rpm. The cell pellet was then resuspended in a volume of 300 µl of culture medium per 50 mg of initial tissue.

Establishment of a Rat Beta Cell Line

300 µl of dissociated cell suspension was next seeded on a poly-L-lysine/laminin coated 1.5 cm$^2$ culture well prepared the day before cell seeding. Briefly, culture dishes were coated with a 100 µg/ml poly-L-lysine (Sigma) solution prepared in sterile water and left for three hours. Then the solution was replaced by a 10 µg/ml laminin (Sigma) solution prepared in RPMI (Invitrogen) medium and left overnight. The laminin was then removed just prior to the cell seeding. In order to discard most of the cells debris, the suspension was left in the well for 15 min at 37° C. The culture medium containing non-sedimented cells and debris was next removed and seeded to a new coated well and the fresh medium was added to the initial well.

For cell selection and establishment of a Beta cell line, after 24 hours of culture, cells were infected in the 1.5 cm$^2$ well with 60 ng of p24 capsid protein of pTRIP ΔU3.RIP405-NEO in 200 µl of culture medium supplemented with 10 µg/ml of DEAE dextran. After 1 hour of infection at 37° C., the medium was replaced by 1 ml of fresh medium. G418 (Sigma) was added in the medium at a final concentration of 1 mg/ml 2 weeks after infection. For the first two weeks of treatment G418 containing medium was renewed every day. During the following weeks of treatment the medium was changed only once a week until disappearance of all cells with a fibroblast type morphology. For cell passage, the culture medium was removed and the attached cells were washed twice in 1×PBS (Invitrogen). An appropriate volume of Trypsin EDTA solution (Eurobio) in added according the surface of the culture plate and left 5 min at 37° C. Fresh medium was added and the cells were mechanically resuspended. For the first 10 passages the cells seeded in coated wells of either equivalent or double surface in order to achieve a two fold dilution. Passage was performed when cell confluence was observed. From passage 11, a ⅖ dilution was performed every week to amplify the cell line.

Establishment of a Human Beta Cell Line

Four different ways have been used in order to obtain Beta cells that are both ready for amplification in culture and have integrated in their genomes the SV40 large T, hTERT and the neomycin resistance gene (FIG. 8).

Graft Dissociation of Human Transplanted Tissues

Highly vascularized regions of the graft that correspond to proliferating Beta cell clusters were microdissected. Such clusters were further dissociated in a two step manner: first chemically then mechanically. Before the chemical dissociation each cluster was divided into 20 to 30 mg pieces and each piece was dissected using a scalpel before treatment with 200 units of collagenase type IV (Worthington) in 500 µl of HBSS (Gibco) for 30 minutes at 37° C. The digest was next centrifuged for 15 min at 4000 rpm and the cells were resuspended in 100% heat-inactivated FCS. The mechanical dissociation consisted of passing the cell suspension several times through needles of 0.8 to 0.4 mm diameter until only small groups or individual cells were obtained. Cells were then centrifuged for 15 minutes at 4000 rpm, resuspended in heat-inactivated FCS and counted.

Cell Infection Before Culture or Sub-Transplantation

Cells were infected in suspension using the procedure described for infecting explants. After infection, cells were centrifuged for 15 minutes at 4000 rpm, then washed in the appropriate culture medium and seeded in a coated Petri dish. For sub transplantation, after the centrifugation step, cells were resuspended in 10 µl of matrigel, placed in a small silicone cylinder 15 minutes at 37° C. for polymerization and were transplanted in scid mice as described above (Castaing et al., 2005b).

Culture Conditions of Human Cells

Human Beta cell lines have been established and are amplified using the following culture medium: DMEM containing 5.5 mM D-Glucose (Invitrogen), 2% BSA fraction V fatty acid free (Roche), 10 mM nicotinamide (Sigma), 50 µM 2-mercaptoethanol (Sigma), 1% penicillin/streptomycin (P/S) (Invitrogen), 5.5 µg/ml human transferrin (Sigma) and 6.7 ng/ml sodium selenite. Cells are grown on culture plates coated as follow. Matrigel from Engelbreth-Holm-Swarm murine sarcoma is diluted 1/100 in DMEN and supplemented with 2.5 µg/ml fibronectin (Sigma) and 1% P/S. This coating solution is added on the culture plates and incubated 1 h at 37° C. in a 5% $CO_2$ saturated atmosphere. Next, the coating medium is removed and cells are seeded directly. Cells are passed with trypsin EDTA (Sigma) at 37° C. for 5 min.

Matrigel is a solubilized basement membrane preparation extracted from the Engelbreth-Holm-Swarm (EHS) sarcoma, which gels at room temperature to form a genuine reconstituted basement membrane. Matrigel is a thermal sensitive gel that is liquid at temperatures below 4° C. This 3-D environment mimics the natural surroundings and microenvironments of cells in vivo.

Establishment of a Human Beta Cell Line.

Grafts are dissociated as described above. 250000 cells per $cm^2$ are seeded on coated plates and 3 days after cells are passed at a ½ dilution. Between passages 2 and 9 cells are passed at a ⅔ dilution then at a ¾ dilution for the next 6 passages and finally cells are amplified at ½ dilution once a week. Cells can be frozen in 90% heat inactivated foetal calf serum and 10% DMSO.

Tissue Preparation for Histological Analysis

Two hours before sacrifice, the transplanted mice were injected intra-peritonealy with 0.5 ml of a 2 mg/ml BrdU solution freshly prepared in 0.9% apyrogen NaCl solution. Tissue fixation was performed by intracardiac perfusion of 4% paraformaldehyde (PFA) freshly prepared in phosphate buffered saline (PBS). Then, different post fixation procedures were applied. For immuno-detection on paraffin sections the perfused tissues were postfixed 6 to 7 hours in 3.7% formaldehyde prepared in water then dehydrated and embedded in paraffin. 4 µm sections were performed and used for the immunofluorescent co-detection for both insulin/Pdx1 and insulin/BrdU. For frozen section, the perfused tissues were postfixed for 2 hours in 4% PFA then cryoprotected in 15% sucrose prepared in PBS for 48 hours. The tissues were next embedded in 7% gelatin, 15% sucrose prepared in PBS, frozen at −50° C. in isopentan and 10 µm sections were performed. Such tissues were used for the immunofluorescent co-detection of insulin/SV40 large T antigen. For in situ hybridization, cryo-sections were performed on as describe above after a 24 hours postfixation period.

Immunohistochemical Procedures on Tissue Sections.

Immunofluorescent staining was performed as previously described (Duvillié et al. Diabetes 2003) using the following antibodies: Rabbit anti Pdx1 polyclonal antibody (1/1000, (Duvillie et al., 2003)); guinea pig anti insulin antibody (1/400, DakoCytomation, Trapped, France); rabbit anti-insulin antibody (1/200, Diasorin); mouse anti-BrdU (1/2, Amersham), mouse anti-SV40 LargeT (1/50, Calbiochem) and mouse anti-Ki67 (1/400). The fluorescent secondary antibodies were fluorescein anti-rabbit antibody (1/200; Jackson Immunoresearch Laboratories); fluorescein anti-mouse antibody (1/200, Immunotech, Marseille) and Texas-red anti-guinea pig antibodies (1/200; Jackson Immunoresearch Laboratories).

Immunofluorescent Detection on RYAS 41 Cell Line 12 mm glass cover slips were coated with poly-L-lysin/laminin in a 1.5 $cm^2$ culture well. 1.2 $10^5$ RYAS41 cells were seeding and cultured for 5 days. Two hours before fixation a 10 µM BrdU solution prepared in 0.9% NaCl was added to the culture medium. Next, the culture medium was removed and cells were fixed in 4% paraformaldehyde (PFA) freshly prepared in phosphate buffered saline (PBS) during either 10 min for insulin/SV40 largeT antigen dual detection or 1 hours for both insulin/pdx1 and insulin/BrdU dual detection. Immunofluorescent staining was performed according to manufacturer's instructions. Primary antisera, include mouse anti SV40 largeT antigen monoclonal antibody (1/50, Calbiochem, Merck Biosciences, San Diego, Calif.), guinea pig anti insulin polyclonal Ab (1/400, DakoCytomation, Trappes, France), rabbit anti Pdx1 polyclonal antibody (1/1000 (Duvillie et al., 2003)) and mouse anti BrdU (1/2, Amersham Biosciences, Uppsala, Sweden). The fluorescent secondary antibodies were fluorescein anti-rabbit antibody (1/200; Jackson Immunoresearch Laboratories); fluorescein anti-mouse antibody (1/200, Immunotech, Marseille) and Texas-red anti-guinea pig antibodies (1/200; Jackson Immunoresearch Laboratories).

Cold In Situ Hybridization (ISH) Coupled with BrdU Immunohistochemical Detection Cold in situ hybridization was performed as described previously (Castaing et al., 2001). The proinsulin probe was prepared as previously described (Basmaciogullari et al., 2000). Plasmids were linearized and used as templates for the synthesis of antisense riboprobes by T3 RNA polymerase (Promega), in the presence of digoxygenin-UTP (Roche diagnostic). Colorimetric revelations were performed with 5-bromo-4-chloro-3-indolyl phosphate (Promega) and nitroblue tetrazolium (Promega) for digoxygenin-UTP. After in situ hybridization, BrdU incorporation was visualized by immunohistochemical analysis. Sections were treated for 45 min at room temperature with 2 N HCl in PBS supplemented with 0.25% gelatin (PGT) and 0.1% Triton X-100 and then were incubated for 48 h at 4° C. with an anti-BrdU antibody (1:500; Becton Dickinson) diluted in PGT supplemented with 1% Triton X-100. The secondary antibody (biotinylated anti-mouse immunoglobulin G; 1:200; Vector) was applied to the slides and detected, after amplification with a streptavidin-biotin-HRP complex (vector), by using diaminobenzidine in the presence of hydrogen peroxide (DAB revelation kit; Vector).

Digital Photographs

Photographs were taken either using a fluorescent microscope (Leica; Leitz, Rockleigh, N.J.) and digitized using a cooled three-chip charge coupled-device camera (Hamamatsu C5810; Hamamatsu, Middlesex, N.J.) or using an Axioskop microscope (Zeiss) and a color vision digital camera (Donpisha).

RNA Isolation, Reverse Transcription and Real-Time-PCR

Total RNA was isolated from E11 rat pancreas, lung and from Ryas 41 using the Quiagen RNeasy microkit (Quiagen). cDNA was prepared using Superscript (Invitrogen) and Quantitative real-time RT-PCR was performed using assays-on-demand kits and an ABI Prism 7300 sequence detector (both from Applied Biosystems, Foster City, Calif.), according to the manufacturers instructions.

RYAS41 and H537 Transplantation in Diabetic Mice

To determine the ability of the RYAS41 rat cell line and H537 human cell line to regulate the glycemia of the diabetic mice, scid mice were injected with a solution of Streptozotocin (STZ; 250 mg/kg of body weight; Sigma-Aldrich) freshly prepared in citrate buffer, that is known to destroy Beta cells. Glucose concentrations were measured on blood collected from the tail vein, using a portable glucose meter (GlucoMen, A. Menarini diagnostics, Firenze, Italy). Two days after STZ injection, mice bearing a blood glucose concentration above 4 g/l were implanted subcutaneously with a 3 week lasting insulin capsule (Sustained Release Insulin Implants; LinShin, Scarborough, Canada) in order to normalize the glycemia before RYAS41 transplantation. Either 16 days after STZ treatment or 22 days after STZ treatment, treated mice were transplanted with $10^6$ RYAS41 cells and $10^6$ H537 cells respectively using the following procedure. Briefly, cells were harvested and centrifuged 10 min a 4° C. The cell pellet was next resuspended in 12 µl of ice cold matrigel (BD Bioscience) and the drop was placed in the silicon cylinder and let at 37° C. to polymerize. Then the cylinder containing the cells was placed under the kidney capsule of STZ treated mice. To confirm the contribution of the RYAS41 or H537 graft to the normalization of blood glucose values in the host mice, grafts were removed by unilateral nephrectomy at the end of the experiment.

Glucose Tolerance Test

Following a 16 hour fast, baseline blood glucose levels (g/l) were measured in tail vein blood from mice using the OneTouch Ultra glucose meter and OneTouch test strips (Life Scan Johnson and Johnson). Glucose (2 mg dextrose/g body weight) in sterile NaCL 0.9% was injected intraperitoneally and blood glucose measured 15, 30, 60, and 120 minutes after injection.

Autoantibody Detection by Indirect Immune-Fluorescence

The H212 graft was frozen in liquid nitrogen, 4 µm sections were performed and places on 10 wells teflon slides (Menzel GmbH). Serial dilutions of sera from diabetic patient or control (1/2 to 1/100) were incubated on the tissue sections in PBS 1× containing 0.5% BSA for 25 min at room temperature. Slides are next washed 3 times 10 min in PBS 1× containing 0.5% BSA and then incubated with a FITC conjugated Rabbit anti-human IgG (1/100, DAKO). After 3 washes the slides are amount in fluoromount (DAKO) and observed under a fluorescence microscope (Leica).

Thus, in a specific embodiment, the invention is directed to a method of in vitro diagnosis of diabetes comprising adding sera from patient and control on tissue sections of Beta cell tumors as defined according to one of claims 8 to 10, and incubation with a labeled anti-human IgG, such as a fluorescent labeled conjugated anti-human IgG to reveal the presence or absence of auto-antibodies associated with diabetes in the sera of said patient and wherein the presence of auto-antibodies is indicative of diabetes.

Autoantibody Detection by Western Blot

Protein extracts from H301 graft were prepared. Briefly, the H410 graft was homogenized with the fast prep bio 101 homogenizer (Biorad) in ice cold Tris 20 mM pH8.0, NaCl 20 mM, triton X-100 0.1% by two 40 sec cycles. The suspension was cleared by centrifugation at 15 000 g during 30 min. The amount of protein was measured by the Bradford method (Biorad). 20 µg of protein extracts were separated on a 10% polyacrilamide SDS PAGE and next transferred to a nitrocellulose membrane (Amersham). The resulting blots were saturated in PBS 1× containing 0.1% Tween 20 and 5% low fat milk for 1 h. 1/50 dilution of sera from control or diabetic patients were next incubated with the blots in saturation solution overnight at 4° C. and washed twice in PBS-Tween. Blots were incubated with an HRP conjugated anti human IgG (1/10000) for 2 h and ECL staining was performed according to manufacturer instruction.

Thus, in this embodiment, the invention relates to a method of in vitro diagnosis of diabetes comprising a western blot of a protein extract of human pancreatic Beta cells according one of claims 8 to 10 incubated with sera of a patient and wherein the presence or absence of auto-antibodies associated with diabetes in the sera of said patient is revealed with labeled anti human IgG, such as HRP conjugated anti human IgG, and wherein the presence of auto-antibodies is indicative of diabetes.

Autoantibody Detection by ELISA 96 wells plates (flat bottom) are coated with human H301 protein extracts (prepared as above) diluted to 1.5 µg/ml in PBS 1× overnight at 4° C. Wells are saturated with PBS 1× containing 5% low fat milk for 2 h. Serial dilutions of sera from control or diabetic patients are incubated in the wells overnight at 4° C. in saturation solution. The wells are rinse 3 times in PBS 1× and next incubated with a dilution of HRP conjugated anti human IgG (1/5000) for 1.5 h at room temperature. After two additional washes in PBS 1× the colorimetric reaction is started in TMB buffer (Sigma) during 1.5 h at room temperature and next the color intensity is read in a microplate spectrophotomer at 450 nm.

Thus, in this embodiment, the invention relates to a method of in vitro diagnosis of diabetes comprising an ELISA test in which wells plates are coated with a protein extract of human pancreatic Beta cells according one of claims 8 to 10 and is incubated with patient and control sera, and wherein the presence or absence of auto-antibodies associated with diabetes in the sera of said patient is revealed with labeled anti human IgG, such as HRP conjugated anti human IgG, and wherein the presence of auto-antibodies is indicative of diabetes.

Example 1: Tumour Formation from Rat Immature Pancreases Transduced with Recombinant Lentiviruses Expressing SV40 LargeT Antigen Under the Control of the Insulin Promoter We previously demonstrated that mature insulin producing cells can be stably modified by transduction of pancreatic progenitors with recombinant lentiviruses expressing eGFP under the control of the insulin promoter (Castaing et al., 2005b). In the present work, we asked whether such an approach could be used to generate rat or human Beta cell lines by transduction of pancreatic progenitors with recombinant lentiviruses expressing the SV40 LargeT antigen under the control of the insulin promoter. We first constructed a lentiviral vector designed to restrict SV40 LargeT antigen expression in Beta cells. We produced recombinant lentiviral vectors (pTRIP ΔU3), pseudotyped with the vesicular stomatitis virus (VSV) G-glycoprotein, that expressed either SV40 LargeT antigen (pTRIP ΔU3.RIP405-SV40 largeT) or eGFP (pTrip ΔU3.RIP405-eGFP) under the control of a 405 bp fragment of the rat insulin promoter.

Such viruses were used to infect immature E13 rat immature pancreases that were next transplanted under the kidney capsule of immunoincompetent Scid mice. One month after transplantation, the grafted tissues were removed and their development was analyzed. One month after transplantation, the size of the grafted tissue was enlarged when tissues were infected with viruses expressing SV40 LargeT antigen when compared to infection with viruses expressing eGFP (FIG. 1, compare panels A and B). When pancreases infected with viruses expressing SV40 LargeT antigen were removed 3 months after transplantation, the size of the tissue was even higher (FIG. 1C). Pancreases infected with viruses expressing either SV40 LargeT antigen or eGFP were next sectioned and insulin expression was analyzed by in situ hybridization. While some insulin-expressing cells were detected in pancreases infected with viruses expressing eGFP, their number was hugely increased in pancreases infected with viruses expressing SV40 LargeT antigen (FIG. 1, compare panels D and F). Proliferation of insulin-expressing cells was next analyzed. While rare insulin-expressing cells developed from pancreases infected with viruses expressing eGFP proliferated, as measured by BrdU incorporation, a large number of insulin-expressing cells developed from pancreases infected with viruses expressing SV40 LargeT antigen incorporated BrdU (FIG. 1, compare panels E and G). Insulin expression derived from pancreases infected with viruses expressing SV40 LargeT antigen was next analyzed at the protein level. As expected, insulin-positive cells expressed SV40 LargeT antigen (FIG. 2, panels A-C). They also expressed Pdx1, a transcription factor crucial for Beta cell development and function (Edlund, 1998) (FIG. 2, panels D-F) and incorporate BrdU (FIG. 2, panels G-I). In conclusion, proliferating Beta cells can be generated by infection of rat immature pancreases infected with viruses expressing SV40 LargeT antigen.

Example 2: Establishment of Rat Pancreatic Beta Cell Lines

To establish pancreatic Beta cell lines, grafts were removed, dissociated and further infected with viruses expressing the neomycin resistance gene under the control of the insulin promoter. This allowed a further selection of insulin-transcribing cells by culture in the presence of G418. The protocol is described in detail in FIG. 3A. Using this approach, different cell lines were established and one of them, RYAS41 was further analyzed. As shown in FIG. 3B, RYAS41 cells expressed insulin and SV40 Large T antigen. They also the nuclear transcription factor Pdx1 and proliferate, based on their capacity to incorporate BrdU. We next analyzed the stage of differentiation of RYAS41 cells. For that purpose, we performed comparisons between RYAS41 cells and pancreas or lung at E17. We first analyzed the expression of Ngn3 and Pax4 2 transcription factors expressed in pancreatic progenitor cells (Apelqvist et al., 1999; Sosa-Pineda et al., 1997) and either absent (Apelqvist et al., 1999) or expressed at very low levels (Brun et al., 2004) in mature Beta cells. As shown in Table 1, RYAS41 cells did not express Ngn3 and express extremely low levels of Pax4.

TABLE 1

Gene expression in RYAS41 compared to E17 pancreas and lung.

| | RYAS 41 | Lung | Pancreas E17 |
| --- | --- | --- | --- |
| Cyclo | 1 | 1 | 1 |
| Ngn3 | 0 | $6.3\ 10^{-4}$ | 1 |
| Pax4 | 0.051 | 0 | 1 |
| Amylase | 0 | 0 | 1 |
| Glucagon | 0.4 | 0 | 1 |
| Insulin | 21.27 | 0 | 1 |
| Pdx1 | 8.85 | 0 | 1 |
| Neuro D1 | 98.12 | 0 | 1 |
| Nkx6.1 | 11.84 | $8.7\ 10^{-3}$ | 1 |
| Pcsk1 | 27.12 | 0.015 | 1 |
| Pcsk2 | 98.42 | 0 | 1 |
| Abcc8 | 38.74 | 0.011 | 1 |
| Snap25 | 18.32 | 0.075 | 1 |
| Rab3A | 36.76 | 1.16 | 1 |
| GK | 11 | 0.036 | 1 |

$C_T$ (threshold cycle) value are normalized to cyclophilin and presented as fold increase compared to E17 rat pancreas that expresses all the genes tested.

We also analyzed the expression of 3 other transcription factors Pdx1, NeuroD1 and Nkx6.1, expressed in mature pancreatic Beta cells. Such transcription factors were expressed in RYAS 41 at high levels when compared to E11 pancreas. We next analyzed the expression of amylase and glucagon, markers of acinar and alpha cells respectively. While amylase expression was absent from RYAS41, low levels of expression of glucagon were detected. Finally, we analyzed the expression of 6 genes important for Beta cell function: Pcsk1 and Pcsk2 that participate in the processing of proinsulin to insulin and C-peptide; Abcc8 that codes for the sulfonyurea receptor; Snap25, the Synaptosomal-associated protein 25 kDa; Rab3A a small G protein, member of the Rab family and glucokinase (GK). All were expressed at extremely high levels, when compared to E17 rat pancreas. Finally, insulin was also enriched in RYAS41 cells when compared to E11 pancreas.

Example 3: Tumour Formation from Human Pancreases Transduced with Recombinant Lentiviruses Expressing Different Transgenes Under the Control of the Insulin Promoter We infected human fetal pancreases with recombinant lentiviruses expressing the SV40 LargeT antigen under the control of the insulin promoter. Such tissues were next transplanted under the kidney capsule of immunoincompetent Scid mice. Four to six month after transplantation, the grafted tissues were removed and their development was analyzed. For that purpose, tissues were sectioned and analyzed by immunohistochemistry. Insulin-positive cells had developed from infected pancreases as previously shown for uninfected pancreases (Castaing et al., 2001), forming islet-like structures (FIG. 4A, E). In such tissues, 2 types of islet-like structures could be found. Some islets contained cells expressing SV40 LargeT antigen, others stained negative for this marker (FIG. 4B, F). Interestingly expression of SV40 LargeT antigen was exclusively found in insulin-positive cells in the infected human pancreas, further demonstrating the specificity of the rat insulin promoter used to control the expression of SV40 LargeT antigen (FIG. 4 B, C). Finally, we noted that the size of the islet-like structure expressing SV40 LargeT antigen that developed from infected tissues was larger than the one that developed from uninfected tissues. This was correlated with the proliferation status of Beta cells that did or did not express SV40 LargeT antigen. Specifically, while SV40 LargeT antigen negative Beta cells stained negative for Ki67, a large number of SV40 LargeT antigen positive Beta cells stained positive for Ki67 (FIG. 4, D, H).

Taken together, such results indicate that proliferating human Beta cells can be generated by infecting human fetal pancreases with lentiviruses expressing SV40 LargeT antigen under the control of the insulin promoter.

At that point (four to six month after transplantation) we never observed any formation of insulinoma, as is the case 3 months after transplantation when rat immature pancreases are infected with the same virus. Moreover, when we dissociated and cultured the infected cells, we were unable to generate cell lines.

However, between 10 and 12 months after transplantation, the glycemia of the mice started to decrease rapidly. When the grafts were removed, we found highly vascularized areas mainly composed of proliferating Beta cells (FIG. 5). Such structures resembled insulinoma-like areas found when infected rat tissues were grafted to Scid mice. Such insulinoma-like structures were next dissected, dissociated, further infected with viruses expressing the neomycin resistance gene under the control of the insulin promoter and cultured in conditions identical to the ones used to generate rat Beta cell lines. Under such conditions, we were unable to generate human Beta cell lines. We also directly infected the cells with viruses expressing the hTert under the control of the insulin promoter and again, using conditions identical to the ones used to generate rat Beta cell lines, we were unable to generate human Beta cell lines. A working hypothesis was that the protocol used to infect cells in vitro was deleterious for cell survival. We thus defined a new strategy for gene transfer into Beta cell tumors.

Example 4: Sub-Grafting Human Fetal Pancreases to Generate Beta Cell Tumors

We first infected human fetal pancreases with lentiviruses expressing SV40 LargeT antigen under the control of the insulin promoter. After 10-12 months, pancreases that had developed insulinoma-like structures were micro-dissected, dissociated and infected with lentiviruses expressing hTert under the control of the insulin promoter and sub-transplanted to new scid mice. We found that under such conditions, after 6 additional months, insulinoma-like structures had developed. Interestingly, under such conditions, the whole graft contained insulin-positive cells that were proliferating (FIG. 5). Acinar cells staining positive for carboxypeptidase A were not detected in such sub-grafts. Taken together, this indicates that this sub-graft approach can be used to successively infect pancreatic tissues. Moreover, it is extremely useful to enrich the tissue in Beta cells and to produce an homogeneous population of Beta cells. Finally, it represents a way to keep human in Scid mice.

In addition, when human fetal pancreases were simultaneously infected with both SV40 LargeT and hTERT lentiviral vectors the insulinoma-like structures developed more rapidly in 5 to 6 months when compared to single infections. Therefore, after co-infection and formation of insulinoma-like structures the grafts were re infected with a lentiviral vector expressing the neomycin resistance gene under the control of the insulin promoter and next sub-transplanted to a new scid mice. Under such conditions, the transplanted tissue formed Beta cell tumors structures within 2-4 months. The cells derived from these grafts contained SV40 LargeT, hTERT and neomycin resistance transgenes.

Example 5: Establishment of Human Pancreatic Beta Cell Lines

To establish human pancreatic Beta cell lines, sub-grafts that contain the either the three transgenes SV40 large T and hTERT were removed and dissociated. In contrast with the protocol used to derive the RYAS41 rat cell line, we found that the G418 selection was not necessary to amplify homogeneous insulin expressing cell population. The amplification by the sub-transplantation process appeared to be sufficient to allow homogeneous cell expansion and that in culture the rare contaminating non Beta cells did not survive. We found that the culture conditions used for amplification of rat Beta cells were not permissive for culture and survival of human Beta cells. Cell lines were derived on matrigel and fibronectin coated plates in a serum free medium containing 5.5 mM glucose, BSA, nicotinamide, 2-mercaptoethanol, human transferin and sodium selenium. As shown on FIG. 7 the first obtained cell line (H357) is positive for insulin and pdx1 immuno-staining with a large proportion of cells co-expressing the Ki67 proliferation marker. Such expression features are stable during 40 passages.

We have been able to generate 11 similar cell lines from independent tumors that were generated by sub-transplantation of 3 initial human immature pancreases. In FIG. 8 A-C the complete genealogy of these 3 initial tumors is presented. Importantly, the number of successive sub-transplantations does not seem to be important to generate a cell line. Indeed H458 cell line was obtained after a single sub-transplantation (FIG. 8C) whereas H492 cell line after 6 successive sub-transplantations (FIG. 8A).

Example 6: Characterization of the Human Beta Cell Lines: Gene Profiling by Quantitative RT-PCR For gene profiling we used our human Beta cell line H522 which is representative of all the cell lines that were derived. We performed comparisons with cDNA prepared from H523 and from adult human islets by quantitative RT-PCR (Table 2).

TABLE 2

Gene expression in H522 human cell line compared to human adult islets.

| | Hyas 522 |
| --- | --- |
| Insuline | 1/3333 |
| pdx | 4,9936 |
| IAPP | 1/8 |
| NeuroD1 | 6,4531 |
| Abcc8 | 1/8 |
| pcsk1 | 1/4 |
| glut2 | 1/400 |
| Kcnj11 | 1/2.4 |
| MafA | 1/24 |
| znt8 | 1/2.7 |

$C_T$ (threshold cycle) value are normalized to cyclophilin and presented as fold increase compared to human adult islets that expresses all the tested genes.

We first found that H523 did not express Carboxypeptidase-A mRNA, a marker of acinar cells normally absent from Beta cells. We next searched in H523 cell line for the expression of genes known to be expressed in mature Beta cells. Interestingly, all genes we looked at were found to be expressed at different levels in our human Beta cell line H523 which is representative of all the cell lines that were derived. We first focused on transcription factors. The transcriptional factor Pdx1 was highly expressed in H523, at a level 5 time higher than the one found in the human islet preparation. The transcription factor MafA was expressed in H523 at a level 24 time lower than the one found in the human islet preparation. We next analyzed the expression of genes coding for proteins implicated in insulin processing and secretion. The proconvertase Pcsk1 that is only found in Beta cells in the adult pancreas was expressed in H523 at a level 4 times lower than the one found in the human islet preparation. Glucose transporter Glut2 was expressed in H523 at a level 400 time lower than the one found in the human islet preparation. Kcnj11 and Abcc8 coding for subunits of the potassium channel that represents targets for drugs such as sulfonylureas, were expressed in H523 at levels 2.4 and 8 times lower than the one found in the human islet preparation. The zinc transporter Znt8 (Slc30a8) whose polymorphism has been recently linked to type 2 diabetes (Sladek et al. 2007) and which represents a new a major autoantigen in human type 1 diabetes (Wenzlau et al. 2007) was expressed in H523 at a level 3 time lower than the one found in the human islet preparation. We next looked at peptides known to be expressed by mature Beta cells. Both IAPP and insulin were expressed by human Beta cell line at levels at levels 8 and 3000 times lower than the one found in the human islet preparation.

Figure 9:
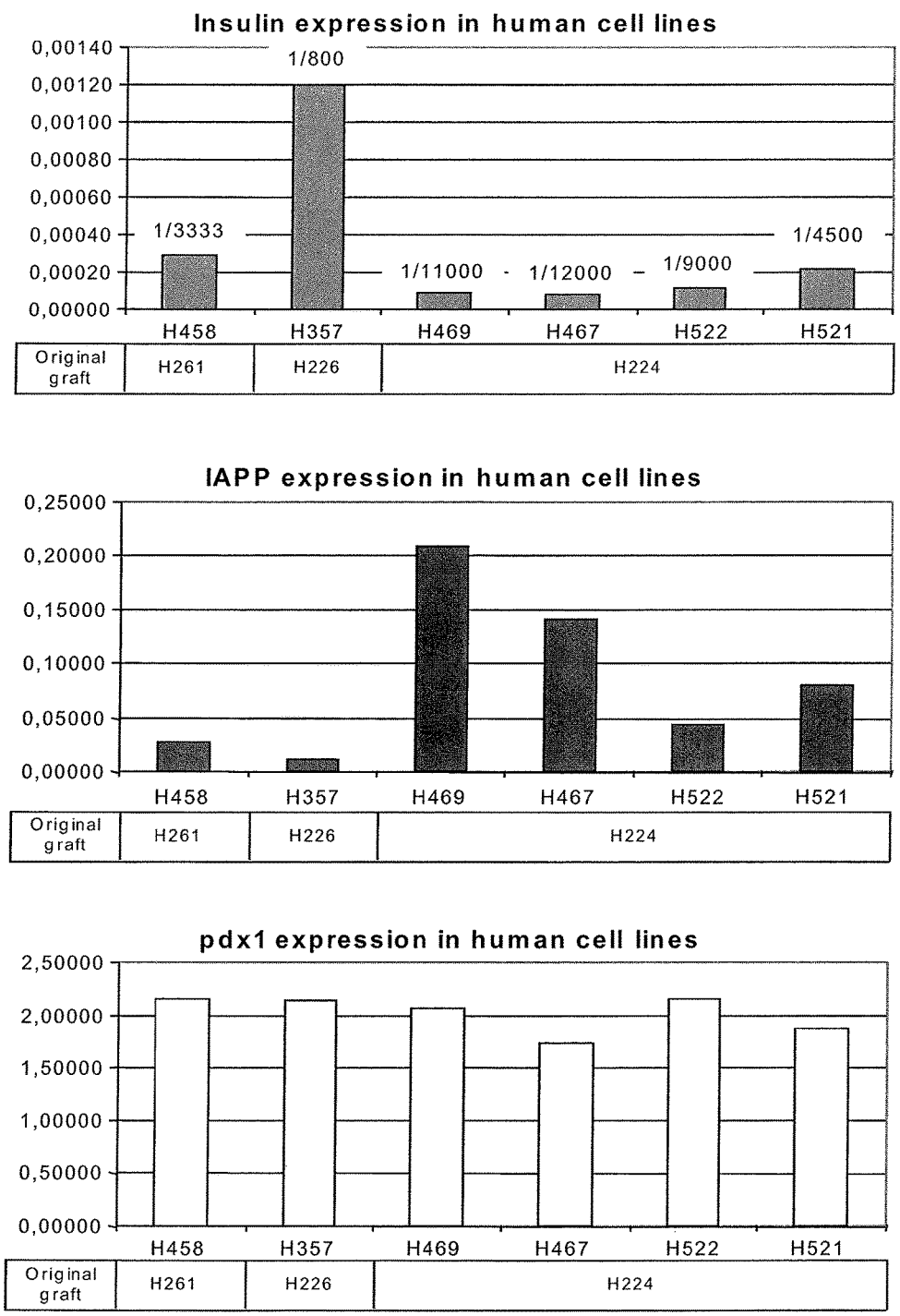

In addition we compared the level of insulin, IAPP and pdx1 expression in 7 of our derived human Beta cell lines with the ones of adult human islets (FIG. 9). We found that pdx1 expression levels were almost identical in all cell lines and similar to that of adult human islets. The cell lines expressed a lower amount of IAPP compared to human islets (from 1/5 to 1/20). In addition the H357 cell line expressed the highest level of insulin which represents 1/800 of expression in an adult human islet.

Example 7: Transplanted RYAS41 Cells Restore Normoglycemia in Diabetic Mice

To define whether RYAS41 cells were functional, scid mice were injected with streptozotocin, a drug known to be toxic for Beta cells. Two days later, the mice were hyperglycemic and insulin capsules were subcutaneously implanted to maintain normoglycemia. were Sixteen days after STZ infection half of the mice (n=7) were transplanted with $10^6$ RYAS41 while the other 7 were used as control. At day 38, insulin secretion by the implanted capsules lasted and glycemia of non transplanted mice was increased and remained high up to the end of the experiments (72 days). On the other hand, glycemia of transplanted mice remained in the normal range (FIG. 7). To demonstrate that glycemia regulation in engrafted mice injected with streptozotocin is indeed due to the transplanted cells, unilateral nephrectomies were performed to remove the grafts and blood glucose concentrations were monitored. As shown in FIG. 7, after removal of the graft by unilateral nephrectomy, at day 66 indicating that in strepotozotocin-treated mice, glycemia was controlled by the grafted cells.

Example 8: Transplanted H357 Human Beta Cell Line can Restore Normoglycemia in Diabetic Mice We performed a similar experiment as described above for the rat RYAS41 cell line. Briefly scid mice were injected with streptozotocin and two day after injection the mice were hyperglycemic and insulin capsules were subcutaneously implanted to maintain normoglycemia. Twenty two days later 10 mice were transplanted with $10^6$ H357 cells and 4 mice were kept as control. As shown in FIG. 11A, two weeks after transplantation the glycemia of the control mice increased and remained high whereas the glycemia of transplanted mice was normalized. The drastic glycemia increase observed after removal of the graft by unilateral nephrectomy demonstrates that glycemia was controlled by the grafted human cells (FIG. 11B).

We further analyzed the in vivo function of the grafted cells by performing glucose tolerance test. 16 hours fasting mice were injected with glucose (2 mg/G of body weight) and glycemia was monitored over a 2 hours period. The glycemia time course presented in FIG. 12 demonstrates that the grafted cell line is able to respond to glucose stimulation of therefore is fully functional in vivo.

Example 9: Human Beta Cell Tumoral Tissue: A Source of Antigenes for Autoantibodies Determination Several arguments are in favour of the autoimmune origin of type 1 diabetes. Among other specific characteristics the presence of auto antibodies has been, for decades, a very strong argument (Bottazzo et al. 1974). For this reason clinicians have used the presence of these auto antibodies as an evidence for type 1 diabetes. Several techniques have been used. In one procedure, antibodies directed toward the Beta cell as a whole are detected (Palmer 1993). This technique is using human pancreas as a source of specific antigens and, by indirect immuno fluorescence, the presence of Islet cell autoantibodies (or ICA) can be demonstrated. These auto antibodies are not antigen specific but recognized only specific constituent of the Beta cell. This technique is the gold standard of antibody determination and has been used for example to demonstrate the high value of ICA to predict the risk of diabetes in a population of relatives of a patient with type 1 diabetes. The presence of ICA at a high titter predicts that this person is at high risk of diabetes. Although this technique is the reference its utilisation has been limited by the difficulty to obtain enough human pancreases to run routinely this ICA determination.

Other techniques have been derived using antigen specific auto antibodies determination. These auto antibodies are anti insulin, anti GAD or anti IA2 and binds specifically to insulin, gutamic acid decarboxylase and a tyrosine phosphatase both enzymes present in the Beta cell. Several commercials techniques are available using labelled antigens (insulin GAD or IA2) for antibody determination in the serum of a patient. These techniques are expensive and are using radioactive material (Falorni et al. 1995).

CONCLUSION

The human tumoral tissue that we have generated contains Beta cells that present very similar properties to human Beta cells. Among other characteristics they contain several genes and proteins characteristic of a human Beta cell. In this respect, this tissue is a new source of Beta cells and tissue containing Beta cells to practice techniques of anti-islet cell autoantibody determination. Thus, the cells as defined above are useful for the diagnostic of diabetes using for examples the following techniques:

Autoantibody Determination by Immuno Fluorescence

As seen in FIG. 13-A a bright fluorescence is observed when the serum of a Type 1 diabetic patient was incubated on tissue sections obtained from tumor H212. This fluorescence was not obtained when the sections were incubated with normal serum.

Autoantibodies Directed Toward Specific Antigens

Protein extract were prepared from H301 tumor. The proteins were separated on SDS PAGE and transferred on a nitrocellulose membrane. As seen in FIG. 13-B, by contrast to what is observed with a normal serum, when a serum of a patient with recently discovered type 1 diabetes was incubated several bands were observed; Two bands correspond to the MW of GAD and IA2 (respectively 65 and 37).

Moreover several other bands could be seen which were not observed when serum from a control was used (FIG. 13-B). These bands are putative auto antigens which react with the serum of the diabetic patient. This material offers therefore a source of proteins to discover new, undescribed antigens from human Beta cells with auto antigenic properties.

Autoantibodies Detection by ELISA

Protein extract from tumor H301 were used to prepare ELISA plates. Elisa tests were performed with sera from control subjects and from 26 patients with recently discovered diabetic patients. These patients were all ICA positive using the classical indirect immuno fluorescent technique method with whole human pancreas. Among this cohort of 26 diabetic patients, 25 were positive with the Elisa method demonstrating the sensitivity of this technique (FIG. 13-C).

REFERENCES

Apelqvist, A., Li, H., Sommer, L., Beatus, P., Anderson, D. J., Honjo, T., Hrabe de Angelis, M., Lendahl, U., and Edlund, H. (1999). Notch signalling controls pancreatic cell differentiation. Nature 400, 877-881.

Asfari, M., Janjic, D., Meda, P., Li, G., Halban, P., and Wolheim, K. (1992). Establishment of 2-mercaptoethanol-dependent differentiated insulin secreting cell lines. Endocrinology 130, 167-178.

Assady, S., Maor, G., Amit, M., Itskovitz-Eldor, J., Skorecki, K. L., and Tzukerman, M. (2001). Insulin production by human embryonic stem cells. Diabetes 50, 1691-1697.

Basmaciogullari, A., Cras-Meneur, C., Czernichow, P., and Scharfmann, R. (2000). Pancreatic pattern of expression of thyrotropin-releasing hormone during rat embryonic development. J Endocrinol 166, 481-488.

Blyszczuk, P., Czyz, J., Kania, G., Wagner, M., Roll, U., St-Onge, L., and Wobus, A. M. (2003). Expression of Pax4 in embryonic stem cells promotes differentiation of nestin-positive progenitor and insulin-producing cells. Proc Natl Acad Sci USA 100, 998-1003.

Bollheimer, L. C., Wrede, C. E., Rockmann, F., Ottinger, I., Scholmerich, J., and Buettner, R. (2005). Glucagon production of the rat insulinoma cell line INS-1-A quantitative comparison with primary rat pancreatic islets. Biochem Biophys Res Commun 330, 327-332.

Bottazzo G-F, Florin-Christensen A, Doniach D. (1974) Islet-cell antibodies in diabetes mellitus with autoimmune polyendocrine deficiencies. *Lancet* 2:1279-1282, Brolen, G. K., Heins, N., Edsbagge, J., and Semb, H. (2005). Signals from the embryonic mouse pancreas induce differentiation of human embryonic stem cells into insulin-producing Beta-cell-like cells. Diabetes 54, 2867-2874.

Brun, T., Franklin, I., St-Onge, L., Biason-Lauber, A., Schoenle, E. J., Wollheim, C. B., and Gauthier, B. R. (2004). The diabetes-linked transcription factor PAX4 promotes {Beta}-cell proliferation and survival in rat and human islets. J Cell Biol 167, 1123-1135.

Castaing, M., Duvillie, B., Quemeneur, E., Basmaciogullari, A., and Scharfmann, R. (2005a). Ex vivo analysis of acinar and endocrine cell development in the human embryonic pancreas. Dev Dyn 234, 339-345.

Castaing, M., Guerci, A., Mallet, J., Czernichow, P., Ravassard, P., and Scharfmann, R. (2005b). Efficient restricted gene expression in Beta cells by lentivirus-mediated gene transfer into pancreatic stem/progenitor cells. Diabetologia 48, 709-719.

Castaing, M., Peault, B., Basmaciogullari, A., Casal, I., Czernichow, P., and Scharfmann, R. (2001). Blood glucose normalization upon transplantation of human embryonic pancreas into Beta-cell-deficient SCID mice. Diabetologia 44, 2066-2076.

D'Amour, K. A., Bang, A. G., Eliazer, S., Kelly, O. G., Agulnick, A. D., Smart, N. G., Moorman, M. A., Kroon, E., Carpenter, M. K., and Baetge, E. E. (2006). Production of pancreatic hormone-expressing endocrine cells from human embryonic stem cells. Nat Biotechnol 24, 1392-1401.

de la Tour, D., Halvorsen, T., Demeterco, C., Tyrberg, B., Itkin-Ansari, P., Loy, M., Yoo, S. J., Hao, E., Bossie, S., and Levine, F. (2001). Beta-cell differentiation from a human pancreatic cell line in vitro and in vivo. Mol Endocrinol 15, 476-483.

Delplanque, A., Coraux, C., Tirouvanziam, R., Khazaal, I., Puchelle, E., Ambros, P., Gaillard, D., and Peault, B. (2000). Epithelial stem cell-mediated development of the human respiratory mucosa in SCID mice. J Cell Sci 113, 767-778.

Demeterco, C., Itkin-Ansari, P., Tyrberg, B., Ford, L. P., Jarvis, R. A., and Levine, F. (2002). c-Myc controls proliferation versus differentiation in human pancreatic endocrine cells. J Clin Endocrinol Metab 87, 3475-3485.

Duvillie, B., Attali, M., Aiello, V., Quemeneur, E., and Scharfmann, R. (2003). Label-retaining cells in the rat pancreas: location and differentiation potential in vitro. Diabetes 52, 2035-2042.

Edlund, E. (1998). Transcribing pancreas. Diabetes 47, 1817-1823.

Efrat, S., Fusco-DeMane, D., Lemberg, H., al Emran, O., and Wang, X. (1995). Conditional transformation of a pancreatic Beta-cell line derived from transgenic mice expressing a tetracycline-regulated oncogene. Proc Natl Acad Sci USA 92, 3576-3580.

Efrat, S., Leiser, M., Surana, M., Tal, M., Fusco-Demane, D., and Fleischer, N. (1993). Murine insulinoma cell line with normal glucose-regulated insulin secretion. Diabetes 42, 901-907.

Efrat, S., Linde, S., Kofod, H., Spector, D., Delannoy, M., Grant, S., Hanahan, D., and Baekkeskov, S. (1988). β cell lines derived from transgenic mice expressing a hybrid insulin gene-oncogene. Proc Natl Acad Sci USA 85, 9037-9041.

Falorni A, Ortqvist E, Persson B, Lernmark A (1995) Radioimmunoassays for glutamic acid decarboxylase (GAD65) and GAD65 autoantibodies using $^{35}S$ or $^3H$ recombinant human ligands. J Immunol Methods 196:89-99.

Gazdar, A., Chick, W., Oie, H., Sims, H., King, D., Weir, G., and Lauris, V. (1980). Continuous, clonal, insulin- and somatostatin-secreting cell lines established from a transplantable rat islet cell tumor. Proc Natl Acad Sci USA 77, 3519-3523.

Gueli, N., Toto, G., Palmieri, G., Carmenini, G., Delfino, A., and Ferrini, U. (1987). In vitro growth of a cell line originated from a human insulinoma. Journal of Experimental and Clinical Cancer Research 4, 281-285.

Halban, P. A., Kahn, S. E., Lemmark, A., and Rhodes, C. J. (2001). Gene and cell-replacement therapy in the treatment of type 1 diabetes: how high must the standards be set? Diabetes 50, 2181-2191.

Hanahan, D. (1985). Heritable formation of pancreatic Beta-cell tumours in transgenic mice expressing recombinant insulin/simian virus 40 oncogenes. Nature 315, 115-122.

Hansson, M., Tonning, A., Frandsen, U., Petri, A., Rajagopal, J., Englund, M. C., Heller, R. S., Hakansson, J., Fleckner, J., Skold, H. N., et al. (2004). Artifactual insulin release from differentiated embryonic stem cells. Diabetes 53, 2603-2609.

Hori, Y., Rulifson, I. C., Tsai, B. C., Heit, J. J., Cahoy, J. D., and Kim, S. K. (2002). Growth inhibitors promote differentiation of insulin-producing tissue from embryonic stem cells. Proc Natl Acad Sci USA 99, 16105-16110.

Ju, Q., Edelstein, D., Brendel, M. D., Brandhorst, D., Brandhorst, H., Bretzel, R. G., and Brownlee, M. (1998). Transduction of non-dividing adult human pancreatic Beta cells by an integrating lentiviral vector. Diabetologia 41, 736-739.

Knaack, D., Fiore, D. M., Surana, M., Leiser, M., Laurance, M., Fusco-DeMane, D., Hegre, O. D., Fleischer, N., and Efrat, S. (1994). Clonal insulinoma cell line that stably maintains correct glucose responsiveness. Diabetes 43, 1413-1417.

Levine, F., Wang, S., Beattie, G., Mally, M., Cirulli, V., Lopez, A., and Hayek, A. (1995). Development of a cell line from human fetal pancreas. Transplantation proceedings 27, 3410.

Levy, L., Broad, S., Zhu, A. J., Carroll, J. M., Khazaal, I., Peault, B., and Watt, F. M. (1998). Optimised retroviral infection of human epidermal keratinocytes: long-term expression of transduced integrin gene following grafting on to SCID mice. Gene Ther 5, 913-922.

Lumelsky, N., Blondel, O., Laeng, P., Velasco, I., Ravin, R., and McKay, R. (2001). Differentiation of Embryonic Stem Cells to Insulin-Secreting Structures Similar to Pancreatic Islets. Science 292, 1389-1394.

Martin, A., Valentine, M., Unger, P., Lichtenstein, C., Schwartz, A. E., Friedman, E. W., Shultz, L. D., and Davies, T. F. (1993). Preservation of functioning human thyroid organoids in the scid mouse: 1. System characterization [see comments]. J Clin Endocrinol Metab 77, 305-310.

Miralles, F., Czernichow, P., and Scharfmann, R. (1998). Follistatin regulates the relative proportions of endocrine versus exocrine tissue during pancreatic development. Development 125, 1017-1024.

Miyazaki, J., Araki, K., Yamato, E., Ikegami, H., Asano, T., Shibasaki, Y., Oka, Y., and Yamamura, K. (1990). Establishment of a pancreatic Beta cell line that retains glucose-inducible insulin secretion: special reference to expression of glucose transporter isoforms. Endocrinology 127, 126-132.

Narushima, M., Kobayashi, N., Okitsu, T., Tanaka, Y., Li, S. A., Chen, Y., Miki, A., Tanaka, K., Nakaji, S., Takei, K., et al. (2005). A human Beta-cell line for transplantation therapy to control type 1 diabetes. Nat Biotechnol 23, 1274-1282.

Palmer J P. (1993) Predicting IDDM: use of humoral markers. Diabetes Rev 1:104-112.

Rajagopal, J., Anderson, W. J., Kume, S., Martinez, O., and Melton, D. A. (2003). Insulin staining of ES cell progeny from insulin uptake. Science 299, 363.

Santerre, R., Cook, R., Criscl, R., Sharp, J., Schidt, R., Williams, D., and Wilson, C. (1981). Insulin synthesis in a clonal cell line of simian virus 40-transformed hamster pancreatic Beta cells. Proc Natl Acad Sci USA 78, 4339-4342.

Sladek R, Rocheleau G, Rung J, Dina C, Shen L, Serre D, Boutin P, Vincent D, Belisle A, Hadjadj S, Balkau B, Heude B, Charpentier G, Hudson T J, Montpetit A, Pshezhetsky A V, Prentki M, Posner B I, Balding D J, Meyre D, Polychronakos C, Froguel P. A genome-wide association study identifies novel risk loci for type 2 diabetes. Nature. 2007 Feb. 22; 445(7130):881-5.

Soldevila, G., Buscema, M., Marini, V., Sutton, R., James, R. F., Bloom, S. R., Robertson, R. P., Mirakian, R., Pujol-Borrell, R., and Bottazzo, G. F. (1991). Transfection with SV40 gene of human pancreatic endocrine cells. J Autoimmun 4, 381-396.

Soria, B., Roche, E., Berna, G., Leon-Quinto, T., Reig, J. A., and Martin, F. (2000). Insulin-secreting cells derived from embryonic stem cells normalize glycemia in streptozotocin-induced diabetic mice. Diabetes 49, 157-162.

Sosa-Pineda, B., Chowdhury, K., Torres, M., Oliver, G., and Gruss, P. (1997). The Pax4 gene is essential for differentiation of insulin-producing β cells in the mammalian pancreas. Nature 386, 399-402.

Thomas, M., Northrup, S. R., and Hornsby, P. J. (1997). Adrenocortical tissue formed by transplantation of normal clones of bovine adrenocortical cells in scid mice replaces the essential functions of the animals' adrenal glands. Nat Med 3, 978-983.

Weissman, A., Gotlieb, L., Colgan, T., Jurisicova, A., Greenblatt, E. M., and Casper, R. F. (1999). Preliminary experience with subcutaneous human ovarian cortex transplantation in the NOD-SCID mouse. Biol Reprod 60, 1462-1467.

Wenzlau J M, Juhl K, Yu L, Moua O, Sarkar S A, Gottlieb P, Rewers M, Eisenbarth G S, Jensen J, Davidson H W, Hutton J C. The cation efflux transporter ZnT8 (Slc30A8) is a major autoantigen in human type 1 diabetes. Proc Natl Acad Sci USA. 2007 Oct. 23; 104(43):17040-5

Zennou, V., Petit, C., Guetard, D., Nerhbass, U., Montagnier, L., and Charneau, P. (2000). HIV-1 genome nuclear import is mediated by a central DNA flap. *Cell* 101, 173-185.

Zufferey, R., Nagy, D., Mandel, R. J., Naldini, L., and Trono, D. (1997). Multiply attenuated lentiviral vector achieves efficient gene delivery in vivo. Nat Biotechnol 15, 871-875.

---

The invention claimed is:

1. A method of preparing a homogenous human beta cell population that is not contaminated by non-beta cells and comprises human beta cells or human beta cell tumors, wherein said human beta cells or human beta cell tumors express insulin and PDX-1, form insulinomas and restore normoglycemia in diabetic SCID mice after transplantation, said method comprising the steps of:

a) transducing or co-transducing immature human pancreases with
      i) a first lentiviral vector expressing SV40 LargeT antigen gene under the control of an insulin promoter and a second lentiviral vector expressing hTert gene under the control of the insulin promoter, or
      ii) a lentiviral vector expressing both SV40 LargeT antigen and hTert genes, wherein expression of both SV40 LargeT antigen and hTert genes are under the control of the insulin promoter,
   thereby producing transduced immature human pancreas cells,
   b) introducing the transduced immature human pancreas cells obtained in step a) into a kidney capsule of a first severe combined immunodeficiency (SCID) mouse, wherein the introduced transduced immature human pancreas cells develop into insulinoma-like structures comprising insulin-producing beta cells in the SCID mouse,
   c) micro-dissecting the insulinoma-like structures obtained in step b), dissociating cells thereof, and optionally transducing said dissociated cells with a lentiviral vector expressing an antibiotic resistance gene under the control of the insulin promoter,
   d) sub-transplanting the cells obtained in step c) into a kidney capsule of a second SCID mouse,
   e) allowing the sub-transplanted cells in step d) to develop and regenerate insulinoma-like structures, wherein said newly developed insulinoma-like structures are enriched in insulin-producing beta cells,
   f) micro-dissecting insulinoma-like structures obtained in step e), dissociating and collecting the cells thereof,
   g) optionally, sub-transplanting the cells obtained in step f) into a kidney capsule of a third SCID mouse, allowing further enrichment and amplification of insulin producing beta cells,
   and optionally repeating steps e), f), and g) until insulin-producing beta cells are produced,
   wherein the sub-transplanting step d), and optionally of step g) lead to a homogenous human beta cell population not contaminated by non-beta cells, and wherein the human beta cells express insulin and PDX-1, form insulinomas and restore normoglycemia in diabetic SCID mice after transplantation.

2. The method according to claim 1, wherein the antibiotic resistance gene in step c) is a neomycin resistance gene.

3. The method according to claim 1, further comprising culturing said homogenous human beta cell population in vitro to establish a human functional beta cell line.

4. The method according to claim 1, further comprising removing the SV40 LargeT antigen and the hTERT genes from the lentiviral vectors used in step a) and the antibiotic resistance gene from the lentiviral vector used in step c).

5. The method according to claim 1, wherein the human beta cells in step d) or g) are cultured in vitro to establish cell lines.

6. The method according to claim 1, wherein the lentiviral vectors used in step a) comprise at least one Lox P site that is targeted by Cre recombinase or at least one FRT site that is targeted by FLP recombinase.

7. The method according to claim 1, wherein the first lentiviral vector expressing SV40 LargeT antigen gene and the second lentiviral vector expressing hTERT gene comprise different site specific recombination sites.

8. The method according to claim 6, wherein a negative selection step is performed after site specific recombination to exclusively select cells in which SV40 LargeT antigen and hTERT, and optionally the antibiotic resistance gene, have been removed.

9. The method according to claim 6, wherein the lentiviral vectors used in step a) include at least one negative selection marker gene.

* * * * *

SEQUENCE LISTING

<160> NUMBER OF SEQ ID NOS: 3

<210> SEQ ID NO 1
<211> LENGTH: 25
<212> TYPE: DNA
<213> ORGANISM: artificial sequence
<220> FEATURE:
<223> OTHER INFORMATION: linker

<400> SEQUENCE: 1
gatcgccccg ggcgggatcc ggtac                                25

```
<210> SEQ ID NO 2
<211> LENGTH: 31
<212> TYPE: DNA
<213> ORGANISM: artificial sequence
<220> FEATURE:
<223> OTHER INFORMATION: Primer BamHI-Neo sens

<400> SEQUENCE: 2
gaggaggatc ccgcatgatt gaacaagatg g                            31

<210> SEQ ID NO 3
<211> LENGTH: 32
<212> TYPE: DNA
<213> ORGANISM: artificial sequence
<220> FEATURE:
<223> OTHER INFORMATION: Primer KpnI-Neo antisens

<400> SEQUENCE: 3
cccaaggtac ccgctcagaa gaactcgtca ag                           32
```